United States Patent
Inouye et al.

(10) Patent No.: US 9,567,623 B2
(45) Date of Patent: Feb. 14, 2017

(54) COELENTERAZINE ANALOGS

(71) Applicant: JNC CORPORATION, Tokyo (JP)

(72) Inventors: Satoshi Inouye, Yokohama (JP); Junichi Sato, Yokohama (JP); Yuiko Miura, Yokohama (JP)

(73) Assignee: JNC CORPORATION, Tokyo (JP)

( * ) Notice: Subject to any disclaimer, the term of this patent is extended or adjusted under 35 U.S.C. 154(b) by 309 days.

(21) Appl. No.: 14/244,953

(22) Filed: Apr. 4, 2014

(65) Prior Publication Data

US 2014/0302539 A1  Oct. 9, 2014

(30) Foreign Application Priority Data

Apr. 8, 2013 (JP) ................ 2013-080734

(51) Int. Cl.
C12Q 1/66 (2006.01)
C07D 487/04 (2006.01)

(52) U.S. Cl.
CPC .............. *C12Q 1/66* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 7,723,502 | B2 | 5/2010 | Coleman et al. |
| 8,557,970 | B2 | 10/2013 | Encell et al. |
| 8,809,529 | B2 | 8/2014 | Klaubert et al. |
| 2002/0102687 | A1 | 8/2002 | Inouye |
| 2014/0223590 | A1 | 8/2014 | Binkowski et al. |

FOREIGN PATENT DOCUMENTS

| | | |
|---|---|---|
| GB | 2425535 A | 11/2006 |
| GB | 2479847 A | 10/2011 |
| JP | 2002320482 A | 11/2002 |
| JP | 2008-000073 A | 1/2008 |
| JP | 4613441 B2 | 1/2011 |
| JP | 2012-525819 A | 10/2012 |
| WO | WO-03/040100 A1 | 5/2003 |
| WO | WO-2004042010 A2 | 5/2004 |
| WO | WO-2010/127368 A1 | 11/2010 |
| WO | WO-2011007314 A1 | 1/2011 |
| WO | WO-2011025980 A1 | 3/2011 |
| WO | WO-2012061529 A1 | 5/2012 |
| WO | WO-2012061530 A2 | 5/2012 |
| WO | WO-2012061530 A3 | 9/2012 |
| WO | WO-2012061530 A8 | 6/2013 |

OTHER PUBLICATIONS

GB Application No. 1400130.3—Search Report mailed Nov. 11, 2014.
GB Application No. 1418471.7—Search Report mailed Jun. 25, 2015.
GB Application No. 1422600.5—Search Report mailed Sep. 15, 2015.
Inouye, et al., "Unconventional secretion of the mutated 19 κDa protein of Oplophorus luciferase (nanoKAZ) in mammalian cells", Biochemical and Biophysical Research Communications, Jul. 11, 2014, vol. 450, , No. 4, pp. 1313-1319.
Satoshi Inouye, et al., "Secretional luciferase of the luminous shrimp *Oplophorus gracilirostris*: cDNA cloning of a novel imidazopyrazinone luciferase[1] ," FEBS Letters 481 (2000), pp. 19-25.
Satoshi Inouye, et al., "C6-Deoxy coelenterazine analogues as an efficient substrate for glow luminescene reaction of nanoKAZ: The mutated catalytic 19 κDa component of *Oplophorus* luciferase," Biochemical and Biophysical Research Communications 437 (2013), pp. 23-28.
Osamu Shimomura, et al., "Properties and Reaction Mechanism of the Bioluminescence System of the Deep-Sea Shrimp *Oplophorus gracilorostris*", Biochemistry, vol. 17, No. 6, 1978, pp. 994-998.
GB Application No. 1403374.0—Search Report mailed Nov. 12, 2014.
Inouye, et al., "Soluble protein expression in *E. coli* cells using IgG-binding domain of protein A as a solubilizing partner in the cold induced system", Biochem. Biophys. Res. Commun., 2008, 376, pp. 448-453.
Inouye, et al., "Codon optimization of genes for efficient protein expression in mammalian cells by selection of only preferred human codons", Proteins Expr. Purif., 2015, 109, pp. 47-54.
Ngo, et al., "Computational Complexity, Protein Structure Prediction, and the Levinthal Paradox", The Protein Folding Problem and Tertiary Structure Prediction, 1994, Merz et al. (ed.), pp. 433 and 492-495.
Mary P. Hall, et al., "Engineered Luciferase Reporter from a Deep Sea Shrimp Utilizing a Novel Imidazopyrazinone Substrate," ACS Chemical Biology, 2012, 7, pp. 1848-1857.
Hideshi Nakamura, et al., "Efficient Bioluminescence of Bisdeoxycoelenterazine with the Luciferase of a Deep-Sea Shrimp *Oplophorus*," Tetrahedron Letters, vol. 38, No. 36, 1997, pp. 6405-6406.

(Continued)

*Primary Examiner* — Paul Holland
(74) *Attorney, Agent, or Firm* — Drinker Biddle & Reath LLP

(57) ABSTRACT

Coelenterazine analogs having luminescence properties different from those of known coelenterazine analogs are desired for various luciferases. The invention provides compounds represented by general formula (1) below.

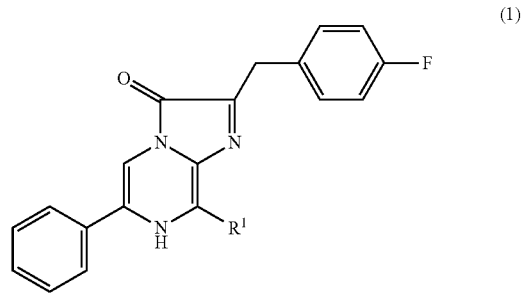

(1)

19 Claims, 3 Drawing Sheets

(56) References Cited

OTHER PUBLICATIONS

Satoshi Inouye, et al., "The Use of *Renilla* Luciferase, *Oplophorus* Luciferase, and Apoaequorin as Bioluminescent Reporter Protein in the Presence of Coelenterazine Analogues as Substrate," Biochemical and Biophysical Research Communications 233, 1997, pp. 349-353.

Satoshi Inouye, et al., "Overexpression, purification and characterization of the catalytic component of *Oplophorus* luciferase in the deep-sea shrimp, *Oplophorus gracilirostris*," Protein Expression & Purification 56, 2007, pp. 261-268.

Satoshi Inouye, et al., "Expression, purification and luminescence properties of coelenterazine-utilizing luciferases from *Renilla, Oplophorus* and *Gaussia*: Comparison of substrate specificity for C2-modified coelenterazines," Protein Expression & Purification 88, 2013, pp. 150-156.

Osamu Shimomura, et al., "Recombinant aequorin and recombinant semi-synthetic aequorins," Biochem. J., 1990, vol. 270, pp. 309-312.

Osamu Shimomura, et al., "Semi-sysnthetic aequorin, An improved tool for the measurement of calcium ion concentration," Biochem. J., 1988, vol. 251, pp. 405-410.

Osamu Shimomura, et al., "Semi-synthetic aequorins with improved sensitivity to $Ca^{2+}$ ions," Biochem. J., 1989, vol. 261, pp. 913-920.

Katsunori Teranishi, "Luminescence of imidazo[1,2- *a*]pyrazin-3(7*H*)-one compounds," Bioorganic Chemistry 35, 2007, pp. 82-111.

Chun Wu, et al., "Chemi- and bioluminescence of coelenterazine analogues with a conjugated group at the C-8 position," Tetrahedron Letters 42, 2001, pp. 2997-3000.

JP Application 2016-001665—Notice of Reasons for Refusal issued Oct. 16, 2016 (including English translation).

Pichler, et al., "Imaging reversal of multidrug resistrance in living mice with bioluminescence: *MDR1* P-glycoprotein transports coelenterazine", Proc. Natl. Acad. Sci., 2004, vol. 101, No. 6, pp. 1702-1707.

SEQUENCE LISTING

<160> NUMBER OF SEQ ID NOS: 9

<210> SEQ ID NO 1
<211> LENGTH: 171
<212> TYPE: PRT
<213> ORGANISM: Artificial sequence
<220> FEATURE:
<223> OTHER INFORMATION: Synthetic Construct

<400> SEQUENCE: 1

Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
            165                 170

<210> SEQ ID NO 2
<211> LENGTH: 516
<212> TYPE: DNA
<213> ORGANISM: Artificial sequence
<220> FEATURE:
<223> OTHER INFORMATION: synthetic DNA

<400> SEQUENCE: 2
atggtcttca ccctggagga cttcgtcggc gactggagac agaccgccgg ctacaacctg     60
gaccaggtcc tggagcaggg cggcgtcagc agcctgttcc agaacctggg cgtcagcgtc    120 accccccatcc agagaatcgt ccttagcggc gagaacggcc tgaagatcga catccacgtc   180
atcatcccct acgagggcct gagcggcgac cagatgggcc agatcgagaa gatcttcaag    240
gtcgtctacc ccgtcgacga ccaccacttc aaggtcatcc tgcactacgg caccctggtc    300
atcgacggcg tcacccccaa catgatcgac tacttcggta gaccctacga gggcatcgcc    360
gtcttcgacg gcaagaagat caccgtcacc ggcaccctgt ggaacggcaa caagatcatc    420
gacgagagac tgatcaaccc cgacggcagc ctgctgttca gagtcaccat caacggcgtc    480
accggctgga gactgtgcga gagaatcctg gcctaa                              516

<210> SEQ ID NO 3
<211> LENGTH: 30
<212> TYPE: DNA
<213> ORGANISM: Artificial sequence
<220> FEATURE:
<223> OTHER INFORMATION: synthetic DNA

<400> SEQUENCE: 3
ggcgaattcg gtgggcttgg cctcggccac                                      30

<210> SEQ ID NO 4
<211> LENGTH: 20

<212> TYPE: DNA
<213> ORGANISM: Artificial sequence
<220> FEATURE:
<223> OTHER INFORMATION: synthetic DNA

<400> SEQUENCE: 4
taatacgact cactataggg                                              20

<210> SEQ ID NO 5
<211> LENGTH: 597
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(597)

<400> SEQUENCE: 5

```
atg gga gtc aaa gtt ctg ttt gcc ctg atc tgc atc gct gtg gcc gag     48
Met Gly Val Lys Val Leu Phe Ala Leu Ile Cys Ile Ala Val Ala Glu
1               5                   10                  15 gcc aag ccc acc gaa ttc aag ctt ggt acc acc atg gtc ttc acc ctg     96
Ala Lys Pro Thr Glu Phe Lys Leu Gly Thr Thr Met Val Phe Thr Leu
            20                  25                  30 gag gac ttc gtc ggc gac tgg aga cag acc gcc ggc tac aac ctg gac    144
Glu Asp Phe Val Gly Asp Trp Arg Gln Thr Ala Gly Tyr Asn Leu Asp
        35                  40                  45 cag gtc ctg gag cag ggc ggc gtc agc agc ctg ttc cag aac ctg ggc    192
Gln Val Leu Glu Gln Gly Gly Val Ser Ser Leu Phe Gln Asn Leu Gly
    50                  55                  60 gtc agc gtc acc ccc atc cag aga atc gtc ctt agc ggc gag aac ggc    240
Val Ser Val Thr Pro Ile Gln Arg Ile Val Leu Ser Gly Glu Asn Gly
65                  70                  75                  80 ctg aag atc gac atc cac gtc atc atc ccc tac gag ggc ctg agc ggc    288
Leu Lys Ile Asp Ile His Val Ile Ile Pro Tyr Glu Gly Leu Ser Gly
                85                  90                  95 gac cag atg ggc cag atc gag aag atc ttc aag gtc gtc tac ccc gtc    336
Asp Gln Met Gly Gln Ile Glu Lys Ile Phe Lys Val Val Tyr Pro Val
            100                 105                 110 gac gac cac cac ttc aag gtc atc ctg cac tac ggc acc ctg gtc atc    384
Asp Asp His His Phe Lys Val Ile Leu His Tyr Gly Thr Leu Val Ile
        115                 120                 125 gac ggc gtc acc ccc aac atg atc gac tac ttc ggt aga ccc tac gag    432
Asp Gly Val Thr Pro Asn Met Ile Asp Tyr Phe Gly Arg Pro Tyr Glu
    130                 135                 140 ggc atc gcc gtc ttc gac ggc aag aag atc acc gtc acc ggc acc ctg    480
Gly Ile Ala Val Phe Asp Gly Lys Lys Ile Thr Val Thr Gly Thr Leu
145                 150                 155                 160 tgg aac ggc aac aag atc atc gac gag aga ctg atc aac ccc gac ggc    528
Trp Asn Gly Asn Lys Ile Ile Asp Glu Arg Leu Ile Asn Pro Asp Gly
                165                 170                 175 agc ctg ctg ttc aga gtc acc atc aac ggc gtc acc ggc tgg aga ctg    576
Ser Leu Leu Phe Arg Val Thr Ile Asn Gly Val Thr Gly Trp Arg Leu
            180                 185                 190 tgc gag aga atc ctg gcc taa                                        597
Cys Glu Arg Ile Leu Ala
        195
```

<210> SEQ ID NO 6
<211> LENGTH: 198
<212> TYPE: PRT
<213> ORGANISM: Artificial sequence

```
<220> FEATURE:
<223> OTHER INFORMATION: Synthetic Construct

<400> SEQUENCE: 6

Met Gly Val Lys Val Leu Phe Ala Leu Ile Cys Ile Ala Val Ala Glu
1               5                   10                  15

Ala Lys Pro Thr Glu Phe Lys Leu Gly Thr Thr Met Val Phe Thr Leu
            20                  25                  30

Glu Asp Phe Val Gly Asp Trp Arg Gln Thr Ala Gly Tyr Asn Leu Asp
        35                  40                  45

Gln Val Leu Glu Gln Gly Gly Val Ser Ser Leu Phe Gln Asn Leu Gly
    50                  55                  60

Val Ser Val Thr Pro Ile Gln Arg Ile Val Leu Ser Gly Glu Asn Gly
65                  70                  75                  80

Leu Lys Ile Asp Ile His Val Ile Ile Pro Tyr Glu Gly Leu Ser Gly
                85                  90                  95

Asp Gln Met Gly Gln Ile Glu Lys Ile Phe Lys Val Val Tyr Pro Val
            100                 105                 110

Asp Asp His His Phe Lys Val Ile Leu His Tyr Gly Thr Leu Val Ile
        115                 120                 125

Asp Gly Val Thr Pro Asn Met Ile Asp Tyr Phe Gly Arg Pro Tyr Glu
    130                 135                 140

Gly Ile Ala Val Phe Asp Gly Lys Lys Ile Thr Val Thr Gly Thr Leu
145                 150                 155                 160

Trp Asn Gly Asn Lys Ile Ile Asp Glu Arg Leu Ile Asn Pro Asp Gly
                165                 170                 175

Ser Leu Leu Phe Arg Val Thr Ile Asn Gly Val Thr Gly Trp Arg Leu
            180                 185                 190

Cys Glu Arg Ile Leu Ala
            195

<210> SEQ ID NO 7
<211> LENGTH: 181
<212> TYPE: PRT
<213> ORGANISM: Artificial sequence
<220> FEATURE:
<223> OTHER INFORMATION: Synthetic Construct

<400> SEQUENCE: 7

Lys Pro Thr Glu Phe Lys Leu Gly Thr Thr Met Val Phe Thr Leu Glu
1               5                   10                  15

Asp Phe Val Gly Asp Trp Arg Gln Thr Ala Gly Tyr Asn Leu Asp Gln
            20                  25                  30

Val Leu Glu Gln Gly Gly Val Ser Ser Leu Phe Gln Asn Leu Gly Val
        35                  40                  45

Ser Val Thr Pro Ile Gln Arg Ile Val Leu Ser Gly Glu Asn Gly Leu
    50                  55                  60

Lys Ile Asp Ile His Val Ile Ile Pro Tyr Glu Gly Leu Ser Gly Asp
65                  70                  75                  80

Gln Met Gly Gln Ile Glu Lys Ile Phe Lys Val Val Tyr Pro Val Asp
                85                  90                  95

Asp His His Phe Lys Val Ile Leu His Tyr Gly Thr Leu Val Ile Asp
            100                 105                 110

Gly Val Thr Pro Asn Met Ile Asp Tyr Phe Gly Arg Pro Tyr Glu Gly
        115                 120                 125

Ile Ala Val Phe Asp Gly Lys Lys Ile Thr Val Thr Gly Thr Leu Trp
```

```
                130               135                140
Asn Gly Asn Lys Ile Ile Asp Glu Arg Leu Ile Asn Pro Asp Gly Ser
145                 150                 155                 160

Leu Leu Phe Arg Val Thr Ile Asn Gly Val Thr Gly Trp Arg Leu Cys
                165                 170                 175

Glu Arg Ile Leu Ala
            180

<210> SEQ ID NO 8
<211> LENGTH: 591
<212> TYPE: DNA
<213> ORGANISM: Oplophorus gracilorostris
<220> FEATURE:
<221> NAME/KEY: CDS
<222> LOCATION: (1)..(591)

<400> SEQUENCE: 8 atg gcg tac tcc act ctg ttc ata att gca ttg acc gcc gtt gtc act      48
Met Ala Tyr Ser Thr Leu Phe Ile Ile Ala Leu Thr Ala Val Val Thr
1               5                   10                  15 caa gct tcc tca act caa aaa tct aac cta act ttt acg ttg gca gat      96
Gln Ala Ser Ser Thr Gln Lys Ser Asn Leu Thr Phe Thr Leu Ala Asp
                20                  25                  30 ttc gtt gga gac tgg caa cag aca gct gga tac aac caa gat caa gtg     144
Phe Val Gly Asp Trp Gln Gln Thr Ala Gly Tyr Asn Gln Asp Gln Val
            35                  40                  45 tta gaa caa gga gga ttg tct agt ctg ttc caa gcc ctg gga gtg tca     192
Leu Glu Gln Gly Gly Leu Ser Ser Leu Phe Gln Ala Leu Gly Val Ser
        50                  55                  60 gtc acg ccc ata cag aaa gtt gta ctg tct ggg gag aat ggg tta aaa     240
Val Thr Pro Ile Gln Lys Val Val Leu Ser Gly Glu Asn Gly Leu Lys
65                  70                  75                  80 gct gat att cat gtc ata ata cct tac gag gga ctc agt ggt ttt caa     288
Ala Asp Ile His Val Ile Ile Pro Tyr Glu Gly Leu Ser Gly Phe Gln
                85                  90                  95 atg ggt cta att gaa atg atc ttc aaa gtt gtt tac ccc gtg gat gat     336
Met Gly Leu Ile Glu Met Ile Phe Lys Val Val Tyr Pro Val Asp Asp
            100                 105                 110 cat cat ttc aag att att ctc cat tat ggt aca ctc gtt att gac ggt     384
His His Phe Lys Ile Ile Leu His Tyr Gly Thr Leu Val Ile Asp Gly
        115                 120                 125 gta aca ccc aac atg att gac tac ttt gga aga cct tac cct gga att     432
Val Thr Pro Asn Met Ile Asp Tyr Phe Gly Arg Pro Tyr Pro Gly Ile
130                 135                 140 gct gta ttt gac ggc aag cag atc aca gtt act gga act ctg tgg aac     480
Ala Val Phe Asp Gly Lys Gln Ile Thr Val Thr Gly Thr Leu Trp Asn
145                 150                 155                 160 ggc aac aag atc tat gat gag agg cta atc aac cct gat ggt tca ctc     528
Gly Asn Lys Ile Tyr Asp Glu Arg Leu Ile Asn Pro Asp Gly Ser Leu
                165                 170                 175 ctc ttc aga gtt act atc aat gga gtc acg gga tgg agg ctt tgc gag     576
Leu Phe Arg Val Thr Ile Asn Gly Val Thr Gly Trp Arg Leu Cys Glu
            180                 185                 190 aac att ctt gcc taa                                                  591
Asn Ile Leu Ala
        195

<210> SEQ ID NO 9
<211> LENGTH: 196
<212> TYPE: PRT
<213> ORGANISM: Oplophorus gracilorostris
```

```
<400> SEQUENCE: 9

Met Ala Tyr Ser Thr Leu Phe Ile Ile Ala Leu Thr Ala Val Val Thr
1               5                   10                  15

Gln Ala Ser Ser Thr Gln Lys Ser Asn Leu Thr Phe Thr Leu Ala Asp
            20                  25                  30

Phe Val Gly Asp Trp Gln Gln Thr Ala Gly Tyr Asn Gln Asp Gln Val
        35                  40                  45

Leu Glu Gln Gly Gly Leu Ser Ser Leu Phe Gln Ala Leu Gly Val Ser
    50                  55                  60

Val Thr Pro Ile Gln Lys Val Val Leu Ser Gly Glu Asn Gly Leu Lys
65                  70                  75                  80

Ala Asp Ile His Val Ile Ile Pro Tyr Glu Gly Leu Ser Gly Phe Gln
                85                  90                  95

Met Gly Leu Ile Glu Met Ile Phe Lys Val Val Tyr Pro Val Asp Asp
                100                 105                 110

His His Phe Lys Ile Ile Leu His Tyr Gly Thr Leu Val Ile Asp Gly
            115                 120                 125

Val Thr Pro Asn Met Ile Asp Tyr Phe Gly Arg Pro Tyr Pro Gly Ile
    130                 135                 140

Ala Val Phe Asp Gly Lys Gln Ile Thr Val Thr Gly Thr Leu Trp Asn
145                 150                 155                 160

Gly Asn Lys Ile Tyr Asp Glu Arg Leu Ile Asn Pro Asp Gly Ser Leu
                165                 170                 175

Leu Phe Arg Val Thr Ile Asn Gly Val Thr Gly Trp Arg Leu Cys Glu
            180                 185                 190

Asn Ile Leu Ala
            195
```

COELENTERAZINE ANALOGS

The priority application, Japanese patent application no. 2013-080734, filed on Apr. 8, 2013, is incorporated by reference herein in its entirety.

SEQUENCE LISTING

The instant application contains a sequence listing which has been submitted in ASCII format via EFS-Web and is hereby incorporated by reference in its entirety. Said ASCII copy, created on Apr. 8, 2013 is named G1047_Sequence_Listings_032814_F.txt and is 14,426 bytes in size.

TECHNICAL FIELD

The present invention relates to coelenterazine analogs, a method for use thereof, and so on.

BACKGROUND ART

Bioluminescence is a phenomenon based on a chemical reaction in vivo, which is called a luciferin (luminescence substrate)-luciferase (enzyme that catalyzes the luminescence reaction) reaction. Numerous studies including the identification of luciferins or luciferases and the elucidation of the luminescence mechanism in a molecular level have been performed for a long time in the country and overseas.

It is known that many marine organisms utilize the compounds having an imidazopyrazinone structure as a luminescence substrate in the bioluminescence reaction.

Among the compounds, coelenterazine (CTZ) is known as the luminescence substrate for *Renilla* luciferase, *Oplophorus* luciferase, *Gaussia* luciferase, etc., or also as the light-emitting substrate of aequorin which is a photoprotein obtained from the jellyfish. Coelenterazine is a compound commonly used as the luminescence substrate for various luciferases and photoproteins, and many findings of CTZ have been accumulated so far (Non-Patent Documents 1 to 9).

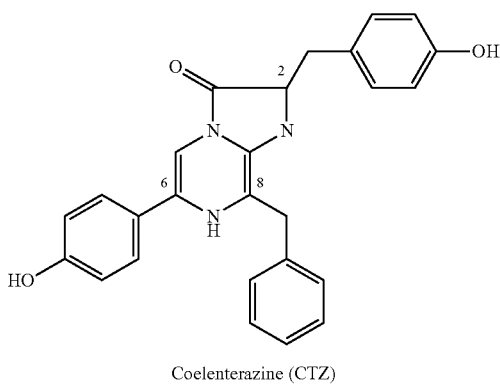 [SMILES: O=C1C(Cc2ccc(O)cc2)NC2=C(Cc3ccccc3)NC(c3ccc(O)cc3)=CN12]

Coelenterazine (CTZ)

As the luminescence reaction system using coelenterazine as a luminescence substrate proceeds only by the luminescence substrate and molecular oxygen, the reporter assays using a luciferase gene have been performed widely.

To date, approximately 50 coelenterazine analogs (CTZ analogs) have been synthesized and the luminescence properties of various luciferases have been studied using them as substrates (Non-Patent Documents 6 to 10).

It is also shown that coelenterazine readily undergoes oxidative degradation in an aqueous solution (Non-Patent Document 9).

*Oplophorus* luciferase is composed of proteins with molecular weights of 35 kDa and 19 kDa. The domain that catalyzes the luminescence reaction is found in the 19 kDa protein. In recent years, a luminescence catalytic domain of 19 kDa having the amino acid mutations has been reported and showed a higher luminescence activity than that of native 19 kDa protein (Non-Patent Document 10).

In particular, *Oplophorus* luciferase and the 19 kD protein which catalyzes the luminescence reaction showed broad substrate specificity than other coelenterazine-type luciferases, indicating that it is difficult to find coelenterazine analogs having 5 times or higher luminescence activity than that of coelenterazine (Non-Patent Documents 6 to 10). Furthermore, when coelenterazine is applied to use for bioluminescence imaging, etc., it has also been desired that coelenterazines are less susceptible to oxidative degradation in an aqueous solution, i.e., a solution for the luminescence reaction.

PRIOR ART REFERENCES

[Non-Patent Document 1] Teranishi K. (2007) *Bioorg. Chem.* 35, 82-111.
[Non-Patent Document 2] Shimomura O. et al. (1990) *Biochem. J.* 270, 309-312.
[Non-Patent Document 3] Shimomura O. et al. (1988) *Biochem. J.* 251, 405-410.
[Non-Patent Document 4] Shimomura O. et al. (1989) *Biochem. J.* 261, 913-920.
[Non-Patent Document 5] Inouye S. & Shimomura O. (1997) *Biochem. Biophys. Res. Commun.* 233, 349-353
[Non-Patent Document 6] Nakamura H. et al. (1997) *Tetrahedron Lett.* 38, 6405-6406.
[Non-Patent Document 7] Wu C. et al. (2001) *Tetrahedron Lett.* 42, 2997-3000.
[Non-Patent Document 8] Inouye S. & Sasaki S. (2007) *Protein Express. Purif.* 56, 261-268.
[Non-Patent Document 9] Inouye S. et al. (2013) *Protein Express. Purif.* 88, 150-156.
[Non-Patent Document 10] Hall M. P. et al. *ACS Chem. Biol.* 2012; 7: 1848-1857.

DISCLOSURE OF THE INVENTION

Problems to be Solved by the Invention

Coelenterazine acts as the luminescence substrate, which is used in numerous luciferases from bioluminescent marine organisms in common. No significant homology is detected in the primary structures among these luciferases and their catalytic sites are not clarified either. It is therefore impossible to precisely design molecules of the luminescence substrate and the luciferase protein and to predict a most suitable luciferin for the luciferase protein. In order to find suitable substrates for individual luciferases, it is necessary to screen them from coelenterazine analogs.

Under the foregoing circumstances, there have been desired coelenterazine analogs showing luminescence properties which are different from those of known coelenterazine analogs.

Means for Solving the Problems

The present inventors have made extensive studies to solve the problems described above and as a result, have found that novel coelenterazine analogs having fluorine instead of hydroxy group on the benzene ring at the position 2 and containing no hydroxy group on the benzene ring at the position 6, of the coelenterazine exhibit different luminescence properties for various luciferases from those of known coelenterazine analogs. The present invention has thus been accomplished.

More specifically, the present invention provides coelenterazine analogs, a method for producing coelenterazine analogs, kits, a luminescence method, etc.

[1] A compound represented by general formula (1) below:

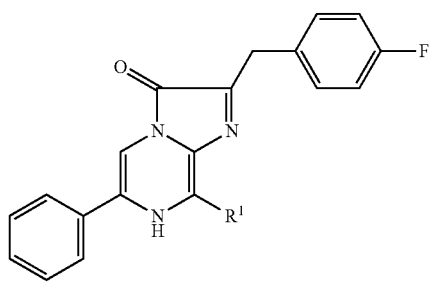

(1)

wherein:

$R^1$ is hydrogen; a substituted or unsubstituted aryl; a substituted or unsubstituted arylalkyl; a substituted or unsubstituted arylalkenyl; an alkyl which may optionally be substituted with an alicyclic group; an alkenyl which may optionally be substituted with an alicyclic group; an alicyclic group; or a heterocyclic group.

[2] The compound according to [1] above, wherein, in general formula (1), $R^1$ is phenyl, p-hydroxyphenyl, benzyl, α-hydroxybenzyl, p-hydroxybenzyl, phenylethyl, phenylvinyl, cyclopentyl, cyclopentylmethyl, cyclohexyl, cyclohexylmethyl, cyclohexylethyl, methyl, ethyl, propyl, 2-methylpropyl, 2-methylpropenyl, adamantylmethyl or thiophen-2-yl.

[3] The compound according to [2] above, wherein $R^1$ is benzyl, α-hydroxybenzyl or p-hydroxybenzyl in general formula (1).

[4] The compound according to [3] above, wherein $R^1$ is benzyl in general formula (1).

[5] A method for producing a compound represented by general formula (1) below:

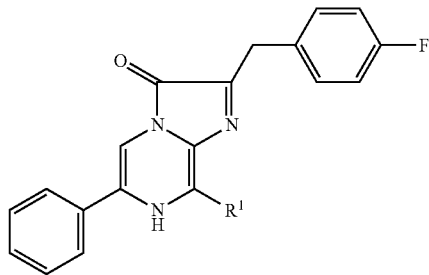

(1)

wherein, $R^1$ is hydrogen; a substituted or unsubstituted aryl; a substituted or unsubstituted arylalkyl; a substituted or unsubstituted arylalkenyl; an alkyl which may optionally be substituted with an alicyclic group; an alkenyl which may optionally be substituted with an alicyclic group; an alicyclic group; or a heterocyclic group, which comprises reacting a compound represented by general formula (2) below:

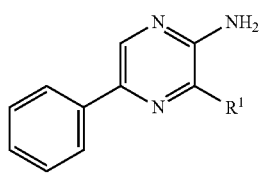

(2)

wherein, $R^1$ is hydrogen; a substituted or unsubstituted aryl; a substituted or unsubstituted arylalkyl; a substituted or unsubstituted arylalkenyl; an alkyl which may optionally be substituted with an alicyclic group; an alkenyl which may optionally be substituted with an alicyclic group; an alicyclic group; or a heterocyclic group, with a compound represented by general formula (3) below:

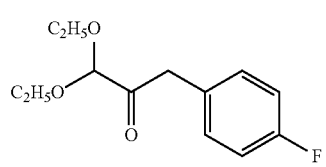

(3)

to give the compound represented by general formula (1).

[6] The method according to [5] above, wherein, in general formula (1), $R^1$ is phenyl, p-hydroxyphenyl, benzyl, α-hydroxybenzyl, p-hydroxybenzyl, phenylethyl, phenylvinyl, cyclopentyl, cyclopentylmethyl, cyclohexyl, cyclohexylmethyl, cyclohexylethyl, methyl, ethyl, propyl, 2-methylpropyl, 2-methylpropenyl, adamantylmethyl or thiophen-2-yl.

[7] The method according to [6] above, wherein $R^1$ is benzyl, α-hydroxybenzyl or p-hydroxybenzyl in general formula (1).

[8] The method according to [7] above, wherein $R^1$ is benzyl in general formula (1).

[9] A kit comprising:

(i) the compound according to any one of [1] to [4] above; and, (ii) at least one selected from a luciferase, a polynucleotide encoding the luciferase, a recombinant vector comprising the polynucleotide, and a transformant comprising the polynucleotide.

[10] The kit according to [9] above, wherein said luciferase is a 19 kDa protein of Oplophorus (Oplophorus sp.) luciferase.

[11] The kit according to [9] above, wherein said luciferase is selected from the group consisting of (a) to (c) below:

(a) a protein comprising the amino acid sequence of SEQ ID NO: 1, (b) a protein comprising an amino acid sequence wherein 1 to 8 amino acids are deleted, substituted, inserted and/or added in the amino acid sequence of SEQ ID NO: 1 and having a luminescence catalytic activity with a luciferin as a substrate, and, (c) a protein comprising an amino acid sequence having at least 95% identity to the amino acid sequence of SEQ ID NO: 1 and having a luminescence catalytic activity with a luciferin as a substrate.

[12] The kit according to [9] above, wherein the polynucleotide encoding said luciferase is a polynucleotide selected from the group consisting of (a) to (d) below:

(a) a polynucleotide comprising a polynucleotide consisting of the nucleotide sequence of SEQ ID NO: 2, (b) a polynucleotide comprising a polynucleotide consisting of a nucleotide sequence in which at least one nucleotide is deleted, substituted, inserted and/or added in the nucleotide sequence of SEQ ID NO: 2 and encoding a protein having a luminescence catalytic activity with a luciferin as a substrate, (c) a polynucleotide comprising a polynucleotide consisting of a nucleotide sequence having at least 90% identity to the nucleotide sequence of SEQ ID NO: 2 and encoding a protein having a luminescence catalytic activity with a luciferin as a substrate, and, (d) a polynucleotide comprising a polynucleotide that hybridizes under stringent conditions to a polynucleotide consisting of a nucleotide sequence complementary to the nucleotide sequence of SEQ ID NO: 2 and encodes a protein having a luminescence catalytic activity with a luciferin as a substrate.

[13] A method for luminescence, which comprises contacting the compound according to any one of [1] to [4] above with a luciferase.

[14] The method according to [13] above, wherein said luciferase is a 19 kDa protein of *Oplophorus* (*Oplophorus* sp.) luciferase.

[15] The method according to [13] above, wherein said luciferase is a protein selected from the group consisting of (a) to (c) below:

(a) a protein comprising the amino acid sequence of SEQ ID NO: 1, (b) a protein comprising an amino acid sequence wherein 1 to 8 amino acids are deleted, substituted, inserted and/or added in the amino acid sequence of SEQ ID NO: 1 and having a luminescence catalytic activity with a luciferin as a substrate, and, (c) a protein comprising an amino acid sequence having at least 95% identity to the amino acid sequence of SEQ ID NO: 1 and having a luminescence catalytic activity with a luciferin as a substrate.

[16] A method for assaying the activity of a sequence associated with promoter regulation, which comprises using a polynucleotide encoding a luciferase as a reporter gene and, as a luminescence substrate, the compound according to any one of [1] to [4] above.

[17] The method according to [16] above, wherein said luciferase is a 19 kDa protein of *Oplophorus* (*Oplophorus* sp.) luciferase.

[18] The method according to [16] above, wherein said luciferase is a protein selected from the group consisting of (a) to (c) below:

(a) a protein comprising the amino acid sequence of SEQ ID NO: 1, (b) a protein comprising an amino acid sequence wherein 1 to 8 amino acids are deleted, substituted, inserted and/or added in the amino acid sequence of SEQ ID NO: 1 and having a luminescence catalytic activity with a luciferin as a substrate, and, (c) a protein comprising an amino acid sequence having at least 95% identity to the amino acid sequence of SEQ ID NO: 1 and having a luminescence catalytic activity with a luciferin as a substrate.

[19] The method according to [16] above, wherein the polynucleotide encoding said luciferase is a polynucleotide selected from the group consisting of (a) to (d):

(a) a polynucleotide comprising a polynucleotide consisting of the nucleotide sequence of SEQ ID NO: 2, (b) a polynucleotide comprising a polynucleotide consisting of a nucleotide sequence in which at least one nucleotide is deleted, substituted, inserted and/or added in the nucleotide sequence of SEQ ID NO: 2 and encoding a protein having a luminescence catalytic activity with a luciferin as a substrate, (c) a polynucleotide comprising a polynucleotide consisting of a nucleotide sequence having at least 90% identity to the nucleotide sequence of SEQ ID NO: 2 and encoding a protein having a luminescence catalytic activity with a luciferin as a substrate, and, (d) a polynucleotide comprising a polynucleotide that hybridizes under stringent conditions to a polynucleotide consisting of a nucleotide sequence complementary to the nucleotide sequence of SEQ ID NO: 2 and encodes a protein having a luminescence catalytic activity with a luciferin as a substrate.

Effects of the Invention

The present invention provides a coelenterazine analog having luminescence properties to various luciferases, which are different from those of known coelenterazine analogs. The coelenterazine analog in a preferred embodiment of the invention serves as a substrate suitable for the mutated 19 kDa protein showing a higher activity than the 19 kDa protein of native *Oplophorus* luciferase which shows broad substrate specificity. The coelenterazine analog in a preferred embodiment of the invention is highly stable in its aqueous solution, compared to coelenterazine.

BEST MODE FOR CARRYING OUT THE INVENTION

Figure 1:
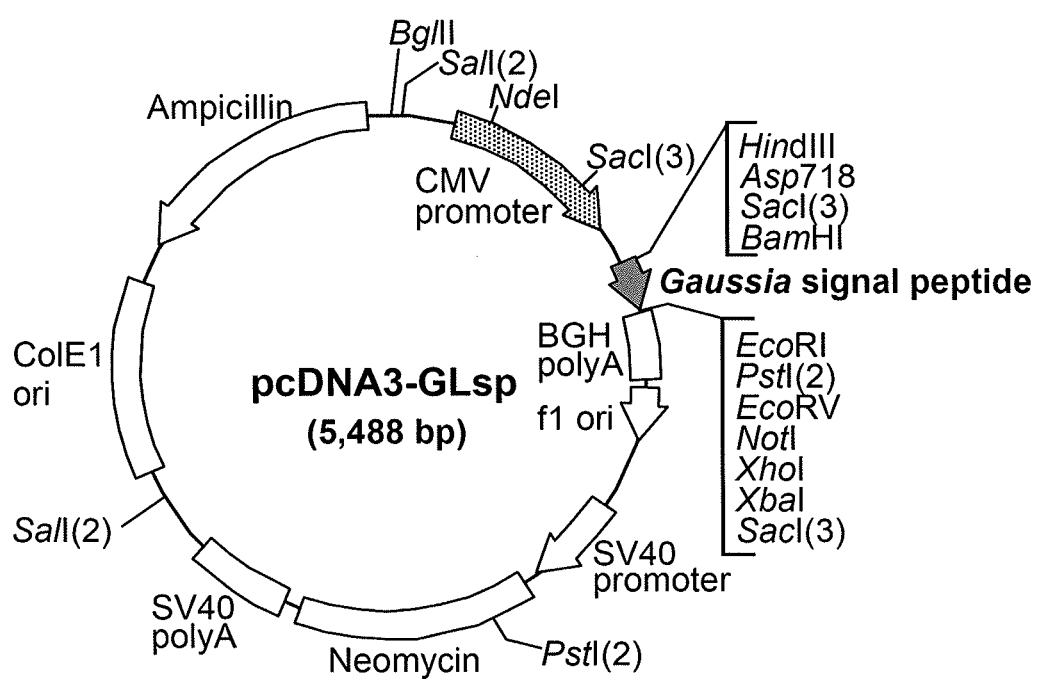
FIG. 1 shows a plasmid map of the expression vector pcDNA3-GLsp having a secretory signal sequence of *Gaussia* luciferase.

Hereinafter the present invention will be described in detail.

1. Coelenterazine Analogs of the Invention

The present invention provides the compounds represented by general formula (1) below (which are sometimes referred to as "the coelenterazine analogs of the present invention" herein).

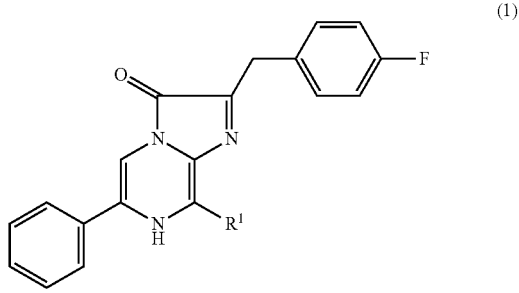

In formula (1):

R$^1$ is hydrogen; a substituted or unsubstituted aryl; a substituted or unsubstituted arylalkyl; a substituted or unsubstituted arylalkenyl; an alkyl which may optionally be substituted with an alicyclic group; an alkenyl which may optionally be substituted with an alicyclic group; an alicyclic group; or a heterocyclic group.

The "substituted or unsubstituted aryl" of R$^1$ is, for example, an aryl having 1 to 5 substituents, or an unsubstituted aryl. The substituent includes, for example, at least one selected from the group consisting of a halogen (e.g. fluorine, chlorine, bromine or iodine), hydroxy, an alkyl having 1-6 carbon atoms, an alkoxyl having 1-6 carbon atoms, amino and a dialkylamino having 1-6 carbon atoms. In some embodiments of the present invention, the substituent is hydroxy. Specific examples of the "substituted or unsubstituted aryl" include phenyl, p-hydroxyphenyl, p-aminophenyl, p-dimethylaminophenyl, etc., preferably, phenyl or p-hydroxyphenyl. In some embodiments of the present invention, the "substituted or unsubstituted aryl" is an unsubstituted aryl, e.g., phenyl.

The "substituted or unsubstituted arylalkyl" of R$^1$ is, for example, an arylalkyl having 7-10 carbon atoms of 1 to 5 substituents, or an arylalkyl having 7-10 carbon atoms. The substituent includes, for example, a halogen (e.g. fluorine, chlorine, bromine or iodine), hydroxy, an alkyl having 1-6 carbon atoms, an alkoxyl having 1-6 carbon atoms, amino and a dialkylamino having 1-6 carbon atoms. The "substituted or unsubstituted arylalkyl" includes, for example, benzyl, α-hydroxybenzyl, p-hydroxybenzyl, p-dimethylaminobenzyl or phenylethyl, and preferably, benzyl, α-hydroxybenzyl, p-hydroxybenzyl or phenylethyl. In some embodiments of the present invention, the "substituted or unsubstituted arylalkyl" is benzyl.

The "substituted or unsubstituted arylalkenyl" of R$^1$ is, for example, an arylalkenyl having 8-10 carbon atoms of 1 to 5 substituents, or an arylalkenyl having 8-10 carbon atoms. The substituent includes, for example, a halogen (e.g. fluorine, chlorine, bromine or iodine), hydroxy, an alkyl having 1-6 carbon atoms, an alkoxyl having 1-6 carbon atoms, amino and a dialkylamino having 1-6 carbon atoms. The "substituted or unsubstituted arylalkenyl" includes, for example, phenylvinyl, p-hydroxyphenylvinyl or p-dimethylaminophenylvinyl. In some embodiments of the present invention, the "substituted or unsubstituted arylalkenyl" is an unsubstituted arylalkenyl, e.g., phenylvinyl.

The "alkyl which may optionally be substituted with an alicyclic group" of R$^1$ includes, for example, an unsubstituted straight or branched alkyl having 1-4 carbon atoms and a straight or branched alkyl having 1-4 carbon atoms, which is substituted with, e.g., 1-10 alicyclic groups. The alicyclic group includes, for example, cyclohexyl, cyclopentyl, adamantyl, cyclobutyl and cyclopropyl. Preferred examples of the alicyclic group are cyclohexyl, cyclopentyl and adamantyl. The "alkyl which may optionally be substituted with an alicyclic group" includes, for example, methyl, ethyl, propyl, 2-methylpropyl, adamantylmethyl, cyclopentylmethyl, cyclohexylmethyl, cyclohexylethyl, cyclobutylmethyl and cyclopropylmethyl, and preferably, methyl, ethyl, propyl, 2-methylpropyl, adamantylmethyl, cyclopentylmethyl, cyclohexylmethyl and cyclohexylethyl. In some embodiments of the present invention, the "alkyl which may optionally be substituted with an alicyclic group" is a straight alkyl which may optionally be substituted with an alicyclic group, e.g., methyl, ethyl, propyl, adamantylmethyl, cyclopentylmethyl, cyclohexylmethyl and cyclohexylethyl.

The "alkenyl which may optionally be substituted with an alicyclic group" includes an unsubstituted straight or branched alkenyl having 2-6 carbon atoms and a straight or branched alkenyl having 2-6 carbon atoms, which is substituted with, e.g., 1-10 alicyclic groups. The alicyclic group includes, for example, cyclohexyl, cyclopentyl, adamantyl, cyclobutyl and cyclopropyl. Preferred examples of the alicyclic group are cyclohexyl, cyclopentyl and adamantyl. The "alkenyl which may optionally be substituted with an alicyclic group" includes, for example, vinyl, 1-propenyl, 2-propenyl, 1-butenyl, 2-butenyl, 3-butenyl and 2-methylpropenyl, and preferably, 2-methylpropenyl.

The "alicyclic group" of R$^1$ includes, for example, cyclohexyl, cyclopentyl, adamantyl, cyclobutyl and cyclopropyl. Preferred examples of the alicyclic group include cyclopentyl and cyclohexyl.

The "heterocyclic group" in R$^1$ includes, for example, a group derived from a 5- to 7-membered ring containing, in addition to carbon atoms, 1 to 3 atoms selected from the group consisting of N, O and S as the atoms constituting the ring and bonded via carbon atoms, a group formed by fusing two or more of such rings and bonded via carbon, and a group formed by fusing such a ring to a benzene ring and bonding via carbon atoms. Examples of the "heterocyclic group" include thiophen-2-yl, 2-furanyl and 4-pyridyl. In some embodiments of the present invention, the "heterocyclic group" is a heterocyclic group containing sulfur, e.g., thiophen-2-yl.

In a preferred embodiment of the present invention, R$^1$ is phenyl, p-hydroxyphenyl, benzyl, α-hydroxybenzyl, p-hydroxybenzyl, phenylethyl, phenylvinyl, cyclopentyl, cyclopentylmethyl, cyclohexyl, cyclohexylmethyl, cyclohexylethyl, methyl, ethyl, propyl, 2-methylpropyl, 2-methylpropenyl, adamantylmethyl or thiophen-2-yl.

In a more preferred embodiment of the present invention, R$^1$ is benzyl. The compound represented by general formula (1) in which R$^1$ is benzyl is the compound shown by formula below (sometimes referred to as "C6d-f-coelenterazine" or "C6d-f-CTZ" herein).

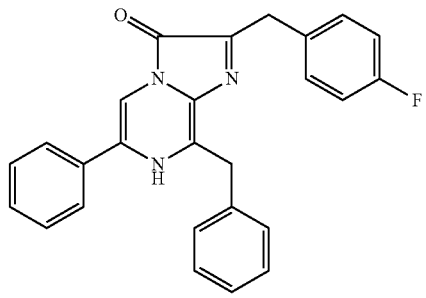

In an embodiment of the present invention, the coelenterazine analogs exhibit luminescence properties different from those of known coelenterazine analogs.

2. Method for Producing Coelenterazine Analog of the Invention

The compounds represented by general formula (1) ("coelenterazine analogs of the present invention") can be produced as follows.

Specifically, the compounds represented by general formula (2) below:

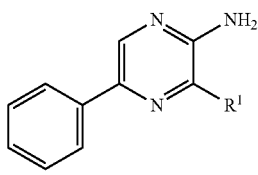

(2)

wherein R¹ is defined as above,
is reacted with the compound represented by general formula (3) below:

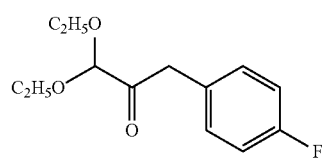

(3)

whereby the compounds represented by general formula (1) can be produced.

The compounds represented by general formula (2) can be produced by known methods. For instance, the compounds represented by general formula (2) can be produced by the method described in Kishi, Y. et al., *Tetrahedron Lett.*, 13, 2747-2748 (1972), or Adamczyk, M. et al., *Org. Prep. Proced. Int*, 33, 477-485 (2001), or a modification thereof. More specifically, the compounds represented by general formula (2) can be produced as follows. That is, first, cyclization of substituted phenylglyoxal aldoximes and glycinonitrile derivatives is carried out using a Lewis acid catalyst to form the pyrazine oxides. Subsequently, the pyrazine oxides are subjected to catalytic hydrogenation using a Raney Ni or the like as a catalyst to produce the compounds. Alternatively, the compounds represented by general formula (2) can be produced by conducting the Suzuki-Miyaura coupling reaction between 2-amino-5-bromopyrazine derivatives and substituted phenylboronic acids or substituted phenylboronic acid pinacol esters.

The compound represented by general formula (3) can be produced by known methods. For example, the compound represented by general formula (3) can be prepared, e.g., by the methods described in Adamczyk, M. et al., *Synth. Commun.*, 32, 3199-3205 (2002), or Baganz, H. & May, H.-J. *Chem. Ber.*, 99, 3766-3770 (1966) and Baganz, H. & May, H.-J. *Angew. Chem., Int. Ed. Eng.*, 5, 420 (1966), or their modifications. More specifically, the compound represented by general formula (3) can be produced as follows. That is, the compound represented by general formula (3) can be produced either by reacting a substituted benzyl Grignard reagent with ethyl diethoxyacetate at a low temperature (−78° C.), or by reacting an α-diazo-α'-substituted phenyl ketone with tert-butyl hypochlorite in ethanol.

Herein, solvents used for the method for producing the compounds of the present invention represented by general formula (1) are not particularly limited and various solvents can be used. Examples of such solvents include dioxane, tetrahydrofuran, ether, methanol, ethanol, water, etc. These solvents can be used alone or as an admixture thereof.

In the method for producing the compounds of the present invention represented by general formula (1), the reaction temperature and reaction time are not particularly limited and are, for example, 0° C. to 200° C. for 1 to 96 hours, room temperature to 150° C. for 3 to 72 hours, or 60° C. to 120° C. for 6 to 24 hours.

3. Protein of the Invention

The proteins of the present invention are mutated proteins of the 19 kDa protein of native *Oplophorus* luciferase, which comprise an amino acid sequence of a polypeptide having an activity substantially equivalent to that of the protein comprising the amino acid sequence of SEQ ID NO: 1.

The "activity substantially equivalent to that of the protein comprising the amino acid sequence of SEQ ID NO: 1" is intended to mean, for example, a luminescence catalytic activity with a luciferin as a substrate (herein sometimes referred to as "luminescence activity"), that is, the activity of catalyzing the reaction that the luciferin (e.g., coelenterazines) is oxidized with oxygen molecules to form oxyluciferin in its excited state. The oxyluciferin formed in the excited state emits visible light to decay to the ground state.

The activity or function can be determined, e.g., by the method described in Inouye, S. & Shimomura, O. (1977) Biochem. Biophys. Res. Commun. 233, 349-353. Specifically, the luminescence catalytic activity can be determined by mixing the protein of the present invention with luciferin to initiate the luminescence reaction and measuring the activity using a luminometer. Devices commercially available, e.g., Luminescencer-PSN AB2200 (manufactured by Atto Co., Ltd.) or Centro 960 luminometer (manufactured by Berthold Inc.) may be used as the luminometer.

The luciferin used in the present invention may be any luciferin, so long as it is a luciferin which serves as a substrate for the protein of the present invention. Specifically, the luciferin used in the present invention includes coelenterazines having an imidazopyrazinone ring as the basic skeleton.

The coelenterazines are intended to mean coelenterazine or analogs thereof (e.g., the coelenterazine analogs of the present invention). The coelenterazines can be synthesized by known methods or are commercially available. The method for producing the coelenterazine analogs of the present invention is as described hereinabove.

The "luminescence catalytic activity with a luciferin as a substrate" is preferably the luminescence catalytic activity with a coelenterazine as a substrate. The "luminescence catalytic activity with a coelenterazine as a substrate" preferably refers to the luminescence catalytic activity with the coelenterazine analog of the present invention as a substrate. More preferably, the "luminescence catalytic activity with the coelenterazine analog of the present invention as a substrate" refers to the luminescence catalytic activity showing a relative maximum luminescence intensity 5 times or higher as compared to coelenterazine, when the coelenterazine analog of the present invention is used as a substrate. Most preferably, when the coelenterazine analog of the present invention is used as a substrate, it is the luminescence catalytic activity showing a relative maximum luminescence intensity 5 times or higher as compared to coelenterazine that provides a continuous luminescence. In terms of the relative maximum luminescence intensity, "5 times or higher" is, for example, 5 to 20 times, 5 to 15 times, 5 to 14 times, 5 to 13 times, 5 to 12 times or 5 to 11 times. The time period for continuous luminescence in the "continuous luminescence" is, for example, 1 minute to 120 minutes, 1 minute to 60 minutes, 1 minute to 30 minutes, 1 minute to 15 minutes, 1 minute to 10 minutes, 1 minute to 5 minutes or 1 minute to 3 minutes.

The "protein which comprise an amino acid sequence of a polypeptide having an activity substantially equivalent to that of the protein comprising the amino acid sequence of SEQ ID NO: 1" is a protein selected from the group consisting of (a) to (c) below.

(a) a protein comprising the amino acid sequence of SEQ ID NO: 1, (b) a protein comprising an amino acid sequence wherein 1 to 8 amino acids are deleted, substituted, inserted and/or added in the amino acid sequence of SEQ ID NO: 1 and having the luminescence catalytic activity with a luciferin as a substrate, and, (c) a protein comprising an amino acid sequence having at least 95% identity to the amino acid sequence of SEQ ID NO: 1 and having the luminescence catalytic activity with a luciferin as a substrate.

As used herein, the "1 to 8 amino acids are deleted, substituted, inserted and/or added" is intended to mean that deletion, substitution, insertion and/or addition of 1 to 8 amino acid residues may occur at any optional and 1 to 8 positions of in the same amino acid sequence.

The range of "1 to 8" in the "amino acid sequence wherein 1 to 8 amino acids are deleted, substituted, inserted and/or added" is, for example, 1 to 8, 1 to 7, 1 to 6 (1 to several), 1 to 5, 1 to 4, 1 to 3, 1 to 2, or 1. In general, the less the number of amino acids deleted, substituted, inserted and/or added, the more preferable. In the deletion, substitution, insertion and addition of the amino acid residues described above, two or more may occur concurrently. Such domains can be acquired using site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

Examples of mutually substitutable amino acid residues are given below. The amino acid residues in the same group can be mutually substituted.
Group A: leucine, isoleucine, norleucine, valine, norvaline, alanine, 2-aminobutanoic acid, methionine, o-methylserine, t-butylglycine, t-butylalanine and cyclohexylalanine;
Group B: aspartic acid, glutamic acid, isoaspartic acid, isoglutamic acid, 2-aminoadipic acid and 2-aminosuberic acid;
Group C: asparagine and glutamine;
Group D: lysine, arginine, ornithine, 2,4-diaminobutanoic acid and 2,3-diaminopropionic acid;
Group E: proline, 3-hydroxyproline and 4-hydroxyproline;
Group F: serine, threonine and homoserine; and,
Group G: phenylalanine and tyrosine.

In the amino acid sequence wherein 1 to 8 amino acids are deleted, substituted, inserted and/or added in the amino acid sequence of SEQ ID NO: 1, it is preferred that none of the following amino acids are deleted or substituted in the amino acid sequence of SEQ ID NO: 1; Glu at position 6, Arg at position 13, Leu at position 20, Leu at position 29, Asn at position 35, Arg at position 45, Ile at position 46, Ile at position 56, Asp at position 70, Gln at position 74, Lys at position 77, Val at position 92, Glu at position 117, Lys at position 126, Ile at position 140 and Arg at position 168.

As used herein, the range of "at least 95%" in the "amino acid sequence having at least 95% identity" is, for example, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the numerical value indicating the identity above is preferably higher. The identity between amino acid sequences or nucleotide sequences can be determined using a sequencing program such as BLAST (see, e.g., Altzshul S. F. et al., J. Mol. Biol. 215, 403 (1990), etc.). When BLAST is used, the default parameters for the respective programs are employed.

The protein of the present invention may be a protein encoded by the polynucleotide of the invention later described.

Preferably, the protein of the present invention is a protein selected from the group consisting of (a) to (c) below.

(a) a protein comprising the amino acid sequence of SEQ ID NO: 1, (b) a protein comprising an amino acid sequence wherein 1 to 4 amino acids are deleted, substituted, inserted and/or added in the amino acid sequence of SEQ ID NO: 1 and having the luminescence catalytic activity with a luciferin as a substrate, and, (c) a protein comprising an amino acid sequence having at least 98% identity to the amino acid sequence of SEQ ID NO: 1 and having the luminescence catalytic activity with a luciferin as a substrate.

More preferably, the protein of the present invention is a protein comprising a polypeptide consisting of the amino acid sequence of SEQ ID NO: 1.

The protein of the invention may further contain an additional peptide sequence at the N terminus and/or the C terminus, preferably at the N terminus. The additional peptide sequence includes, for example, at least one peptide sequence selected from the group consisting of a peptide sequence for promoting translation, a peptide sequence for purification, a secretory signal peptide sequence, a peptide sequence for expressing the protein of the invention as a soluble protein and an epitope sequence capable of recognizing an antibody. The additional peptide sequence is preferably a peptide sequence for purification and/or a secretory signal peptide sequence. In another preferred embodiment of the present invention, the additional peptide sequence is at least one selected from the group consisting of a peptide sequence for purification, a secretory signal peptide sequence, and a sequence for expressing the protein of the present invention as a soluble protein.

The protein of the present invention may further contain a linker sequence for restriction enzyme sites.

Peptide sequences used in the art can be used as the peptide sequence for promoting translation. The peptide sequence for promoting translation includes, for example, a TEE sequence.

Peptide sequences used in the art can be used as the peptide sequence for purification. The peptide sequence for purification includes, for example, a histidine tag sequence having a consecutive amino acid sequence of at least 4 histidine residues, preferably at least 6 histidine residues, an amino acid sequence with a binding domain of glutathione S-transferase into glutathione, the amino acid sequence of Protein A and an avidin tag sequence.

The secretory signal peptide is intended to mean a peptide region which plays a role of transporting a protein bound to the secretory signal peptide across a cell membrane. Amino acid sequences of such secretory signal peptides and nucleic acid sequences encoding the same are well known in the art and reported (see, e.g., von Heijine G (1988) Biochim. Biohys. Acta 947: 307-333, von Heijine G (1990) J. Membr. Biol. 115: 195-201). Specific examples of the secretory signal peptides include the secretory signal peptide from outer membrane protein A of *Escherichia coli* (OmpA)

(Ghrayeb, J. et al. (1984) EMBO J. 3:2437-2442), the secretory signal peptide from *Vibrio cholerae*-derived cholera toxin and the secretory signal peptide of *Gaussia* luciferase used in EXAMPLES later described.

The peptide sequence for expressing the protein of the present invention as a soluble protein includes, for example, a polypeptide represented by formula $(Z)_n$ (ZZ domain in particular). Amino acid sequences of the polypeptide represented by formula $(Z)_n$ and nucleic acid sequences encoding the same include those described in Japanese Patent Application KOKAI No. 2008-99669, and the like.

As the linker sequence for a restriction enzyme site, there can be used peptide sequences used in the art.

In some embodiments of the present invention, the protein includes a protein comprising a polypeptide consisting of the amino acid sequence of SEQ ID NO: 6 or SEQ ID NO: 7.

The method for obtaining the protein of the invention is not particularly limited. The protein of the invention may be a protein synthesized by chemical synthesis, or a recombinant protein produced by a genetic engineering technique. If the protein of the invention is to be chemically synthesized, synthesis may be carried out by, for example, the Fmoc (fluorenylmethyloxycarbonyl) method or the tBoc (t-butyloxycarbonyl) method. Also, peptide synthesizers available from, for example, Advanced ChemTech, PerkinElmer, Pharmacia, Protein Technology Instrument, Synthecell-Vega, PerSeptive, Shimadzu Corporation, etc. may be used for chemical synthesis. Where the protein of the invention is to be produced by a genetic engineering technique, the protein may be produced by a conventional genetic recombination technique. More specifically, the protein of the invention may be produced by inserting a polynucleotide (e.g., a DNA) encoding the protein of the invention into a suitable expression system.

4. Polynucleotide of the Invention

The present invention also provides a polynucleotide encoding the protein of the invention described above. The polynucleotide of the invention may be any polynucleotide as long as it comprises a nucleotide sequence encoding the protein of the invention, although a DNA is preferred. Examples of DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a reverse transcription polymerase chain reaction (hereinafter abbreviated as RT-PCR) using the total RNA or mRNA fraction prepared from the cell or tissue described above.

Specifically, the polynucleotide of the invention is any one of the polynucleotides selected from the group consisting of (a) to (d) below.

(a) a polynucleotide comprising a polynucleotide consisting of the nucleotide sequence of SEQ ID NO: 2, (b) a polynucleotide comprising a polynucleotide encoding a protein consisting of a nucleotide sequence in which at least one nucleotide is deleted, substituted, inserted and/or added in the nucleotide sequence of SEQ ID NO: 2 and having the luminescence catalytic activity with a luciferin as a substrate, (c) a polynucleotide comprising a polynucleotide encoding a protein consisting of a nucleotide sequence having at least 90% identity to the nucleotide sequence of SEQ ID NO: 2 and having the luminescence catalytic activity with a luciferin as a substrate, and, (d) a polynucleotide comprising a polynucleotide that hybridizes under stringent conditions to a polynucleotide consisting of a nucleotide sequence complementary to the nucleotide sequence of SEQ ID NO: 2 and encoding a protein having the luminescence catalytic activity with a luciferin as a substrate.

As used herein, the "luminescence catalytic activity with a luciferin as a substrate" is defined as above.

The "nucleotide sequence in which at least one nucleotide is deleted, substituted, inserted and/or added" is intended to mean that deletion, substitution, insertion and/or addition of one or more nucleotides may occur at any optional and one or more positions in the same nucleotide sequence.

The range of "at least one" in the "nucleotide sequence in which at least one nucleotide is deleted, substituted, inserted and/or added" is, for example, 1 to 20, 1 to 15, 1 to 10, 1 to 9, 1 to 8, 1 to 7, 1 to 6 (1 to several), 1 to 5, 1 to 4, 1 to 3, 1 to 2, or 1. In general, the less the number of nucleotides deleted, substituted, inserted and/or added, the more preferable. In the deletion, substitution, insertion and addition of the nucleotides described above, two or more may occur at the same time. Such domains can be acquired using site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," "Proc. Natl. Acad. Sci. USA, 82, 488 (1985)," etc.

A polynucleotide, in which one or more nucleotides are deleted, substituted, inserted and/or added in a certain nucleotide sequence, can be obtained by using a site-specific mutagenesis technique (cf., e.g., Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985) and Kunkel, Methods Enzymol. 85, 2763-2766 (1988)), methods using amber mutation (cf., e.g., the gapped duplex method, Nucleic Acids Res. 12, 9441-9456 (1984)), etc.

Alternatively, such mutation may be introduced into the polynucleotide by PCR using a set of primers bearing on the respective 5' ends a sequence in which the target mutation (deletion, addition, substitution and/or insertion) has been introduced (see, e.g., Ho S, N. et al., Gene 77, 51 (1989), etc.).

Also, the polynucleotide encoding a partial protein fragment, which is one type of deletion mutants, can be obtained using as the primers an oligonucleotide having a sequence which matches the nucleotide sequence at the 5' end of the region encoding the partial fragment to be produced in the polynucleotide encoding the protein and an oligonucleotide having a sequence complementary to the nucleotide sequence at the 3' end thereof, and performing PCR using a polynucleotide encoding the protein as a template.

The range of "90% or more" in the "nucleotide sequence having at least 90% identity" is, for example, 90% or more, 91% or more, 92% or more, 93% or more, 94% or more, 95% or more, 96% or more, 97% or more, 98% or more, 99% or more, 99.1% or more, 99.2% or more, 99.3% or more, 99.4% or more, 99.5% or more, 99.6% or more, 99.7% or more, 99.8% or more, or 99.9% or more. In general, the greater the numerical value of the identity above, the more preferable. The identity between amino acid sequences or nucleotide sequences can be determined using a sequencing program such as BLAST (see, e.g., Altzshul, S.

F. et al., J. Mol. Biol., 215, 403 (1990), etc.) or the like. When BLAST is used, the default parameters for the respective programs are employed.

That "polynucleotide that hybridizes under stringent conditions" is intended to mean a polynucleotide (e.g., DNA) which is obtained by, for example, colony hybridization, plaque hybridization or Southern hybridization using as a probe all or part of the polynucleotide consisting of a nucleotide sequence complementary to the nucleotide sequence of SEQ ID NO: 2. Specifically, the polynucleotide is a polynucleotide which can be identified by performing hybridization at 65° C. in the presence of 0.7 to 1.0 mol/L NaCl using a filter on which the polynucleotide from a colony or plaque is immobilized, then washing the filter at 65° C. with an SSC (saline-sodium citrate) solution having a concentration of with 0.1- to 2 times (1×SSC solution is composed of 150 mmol/L sodium chloride and 15 mmol/L sodium citrate).

Hybridization may be performed in accordance with modifications of the methods described in experimental manuals, e.g., Sambrook J. et al., Molecular Cloning: A Laboratory Manual, Third Edition, Cold Spring Harbor Laboratory Press (2001), Ausbel F. M. et al., Current Protocols in Molecular Biology, Supplement 1-38, John Wiley and Sons (1987-1997), Glover D. M. and Hames B. D., DNA Cloning 1: Core Techniques, A practical Approach, Second Edition, Oxford University Press (1995), etc.

The "stringent conditions" may refer to any of less stringent conditions, moderately stringent conditions and highly stringent conditions. The "less stringent conditions" are, for example, the conditions under 5×SSC, 5×Denhardt's solution, 0.5% (w/v) SDS and 50% (v/v) formamide at 32° C. The "moderately stringent conditions" are, for example, the conditions under 5×SSC, 5×Denhardt's solution, 0.5% (w/v) SDS and 50% (v/v) formamide at 42° C. The "highly stringent conditions" are, for example, the conditions under 5×SSC, 5×Denhardt's solution, 0.5% (w/v) SDS and 50% (v/v) formamide at 50° C. The more stringent the conditions are, the higher the complementarity required for double strand formation. Specifically, for example, under these conditions, a polynucleotide (e.g., a DNA) of higher homology is expected to be obtained efficiently at higher temperatures, although multiple factors are involved in hybridization stringency, including temperature, probe concentration, probe length, ionic strength, time and base concentration, etc.; those skilled in the art may appropriately choose these factors to realize a similar stringency.

Where a kit commercially available is used for the hybridization, for example, Alkphos Direct Labeling Reagents (manufactured by Amersham Pharmacia) may be used. In this case, incubation with a labeled probe is performed overnight in accordance with the protocol attached to the kit, the membrane is then washed with a primary wash buffer containing 0.1% (w/v) SDS at 55° C. Thus, the hybridized DNA can be detected.

Other polynucleotides that are capable of hybridization include, as calculated by a sequencing program such as BLAST or the like using the default parameters, DNAs having an identity of approximately 60% or more, 65% or more, 70% or more, 75% or more, 80% or more, 85% or more, 88% or more, 90% or more, 92% or more, 95% or more, 97% or more, 98% or more, 99% or more, 99.3% or more, 99.5% or more, 99.7% or more, 99.8% or more, or 99.9% or more, to the polynucleotide encoding the polynucleotide consisting of the nucleotide sequence of SEQ ID NO: 2. The identity between nucleotide sequences can be determined using the method described above.

In a preferred embodiment of the invention, the polynucleotide is a polynucleotide selected from the group consisting of (a) to (d) below.

(a) a polynucleotide comprising a polynucleotide consisting of the nucleotide sequence of SEQ ID NO: 2, (b) a polynucleotide comprising a polynucleotide consisting of a nucleotide sequence in which 1 to 20 nucleotides are deleted, substituted, inserted and/or added in the nucleotide sequence of SEQ ID NO: 2 and encoding a protein having the luminescence catalytic activity with a luciferin as a substrate, (c) a polynucleotide comprising a polynucleotide consisting of a nucleotide sequence having at least 95% identity to the nucleotide sequence of SEQ ID NO: 2 and encoding a protein having the luminescence catalytic activity with a luciferin as a substrate, and, (d) a polynucleotide comprising a polynucleotide that hybridizes under stringent conditions to a polynucleotide consisting of a nucleotide sequence complementary to the nucleotide sequence of SEQ ID NO: 2 and encodes a protein having the luminescence catalytic activity with a luciferin as a substrate.

In a still preferred embodiment of the invention, the polynucleotide is a polynucleotide selected from the group consisting of (a) to (c) below.

(a) a polynucleotide comprising a polynucleotide consisting of the nucleotide sequence of SEQ ID NO: 2, (b) a polynucleotide comprising a polynucleotide consisting of a nucleotide sequence in which at least one nucleotide is deleted, substituted, inserted and/or added in the nucleotide sequence of SEQ ID NO: 2 and encoding a protein having the luminescence catalytic activity with a luciferin as a substrate, (c) a polynucleotide comprising a polynucleotide consisting of a nucleotide sequence having at least 98% identity to the nucleotide sequence of SEQ ID NO: 2 and encoding a protein having the luminescence catalytic activity with a luciferin as a substrate.

In a particularly preferred embodiment of the invention, the polynucleotide is a polynucleotide comprising a polynucleotide consisting of the nucleotide sequence of SEQ ID NO: 2.

The polynucleotide of the present invention may further contain a polynucleotide comprising a polynucleotide encoding an additional peptide sequence. The additional peptide sequence includes, for example, at least one peptide sequence selected from the group consisting of a peptide sequence for promoting translation, a peptide sequence for purification, a secretory signal peptide sequence, a peptide sequence for expressing the fusion protein of the invention as a soluble protein and an epitope sequence capable of recognizing an antibody.

The polynucleotide of the present invention may further contain a polynucleotide encoding the linker sequence for restriction enzyme sites.

Polynucleotides comprising polynucleotides encoding the peptide sequences for promoting translation which are used in the art can be employed as the polynucleotide comprising a polynucleotide encoding the peptide sequence for promoting translation. Examples of the peptide sequence for promoting translation include those described above.

Polynucleotides comprising nucleotide sequences encoding the peptide sequences for purification which are used in the art can be employed as the polynucleotide comprising a nucleotide sequence encoding the peptide sequence for purification. Examples of the peptide sequence for purification include those described above.

Polynucleotides comprising nucleic acid sequences encoding secretory signal peptides which are known in the art can be employed as the polynucleotide encoding the secretory signal peptide. Examples of the secretory signal peptide include those described above.

Polynucleotides comprising nucleic acid sequences encoding peptides for expressing as soluble proteins peptide sequences which are known in the art can be employed as the polynucleotide encoding the peptide sequence for expressing the protein of the invention as a soluble protein. Examples of the peptide for expressing the protein of the invention as a soluble protein include those described above.

Polynucleotides comprising nucleotide sequences encoding linker sequences which are used in the art can be employed as the polynucleotide encoding the linker sequence for restriction enzyme sites.

In some embodiments of the invention, the polynucleotide is a polynucleotide comprising a polynucleotide consisting of the nucleotide sequence of SEQ ID NO: 5.

5. Method for Producing Calcium-Binding Photoprotein

The calcium-binding photoprotein of the invention can be produced or regenerated by contacting the coelenterazine analog of the invention with the apoprotein of the calcium-binding photoprotein thereby to obtain the calcium-binding photoprotein.

As used herein, the term "contact" is intended to mean that the coelenterazine analog of the invention and the apoprotein of the calcium-binding photoprotein are allowed to exist in the same reaction system, and includes, for example, the apoprotein of the calcium-binding photoprotein being added to a container charged with the coelenterazine analog of the invention, the coelenterazine analog of the invention being added to a container charged with the apoprotein of the calcium-binding photoprotein, and the coelenterazine analog of the invention being mixed with the apoprotein of the calcium-binding photoprotein. In one embodiment of the present invention, the contact is carried out at a low temperature in the presence of a reducing agent (e.g., mercaptoethanol or dithiothreitol) and oxygen. More specifically, the photoprotein of the present invention can be produced or regenerated by the methods described in, e.g., Shimomura, O. et al. Biochem. J. 251, 405-410 (1988) and Shimomura, O. et al. Biochem. J. 261, 913-920 (1989). The calcium-binding photoprotein of the present invention is present in such a state that a complex is formed between the peroxide of the coelenterazine analog generated from the coelenterazine analog of the invention and molecular oxygen and the apoprotein. Calcium ions are bound to the complex above to generate instantaneous luminescence and form the coelenteramide analog, which is the oxide of the coelenterazine analog, and carbon dioxide. The complex above is sometimes referred to as "the calcium-binding photoprotein of the present invention."

The apoprotein used to produce the calcium-binding photoprotein of the present invention may be collected from natural sources or produced by genetic engineering. In addition, the apoprotein may be any mutant which amino acid sequence is mutated from the natural sequence by gene recombination technology as long as it is capable of producing the calcium-binding photoprotein. Specific examples of the apoprotein include apoaequorin, apoclytin-I, apoclytin-II, apobelin, apomitrocomin, apomineopsin, apobervoin, and mutated proteins thereof. In some embodiments of the present invention, the apoprotein is apoaequorin, apobelin, apoclytin-I, apoclytin-II or mitrocomin, or mutated proteins, etc., preferably, apoaequorin or its mutated protein. These apoproteins may be produced by known methods or a modification of these methods. Alternatively, various products are commercially available from SNC Corporation and these commercial products may be used as well.

6. Use of Coelenterazine Analogs of the Invention

Use of Detection Marker as Luminescence Substrate by Luminescence

The coelenterazine analog of the present invention can be used as a detection marker by luminescence. The coelenterazine analog of the present invention can be used as a luminescence substrate for the detection marker to detect a target analyte in immunoassay, hybridization assay, etc.

The detection marker of the invention may also be used, for example, by expressing a luciferase or the apoprotein of calcium-binding photoprotein (hereinafter sometimes referred to as "luciferase, etc.") as a fusion protein to the target protein, inserting the fusion protein into a cell by means of microinjection, etc. and contacting the cell with the coelenterazine analog of the invention, thereby to determine distribution of the target protein described above. As used herein, the term "contact" is intended to mean that a cell and the coelenterazine analog of the invention are allowed to be present in the same culture system or reaction system, and includes, for example, the coelenterazine analog of the invention being added to a culture container charged with a cell, a cell being mixed with the coelenterazine analog of the invention, and a cell being cultured in the presence of the coelenterazine analog of the invention. Such distribution of the target protein, etc. may also be determined by utilizing a detection method such as luminescence imaging, etc. In addition to the insertion into a cell by means of microinjection, etc., the luciferase, etc. may also be expressed in a cell and provided for use.

The luciferase may be collected from natural sources or produced by genetic engineering. Furthermore, the luciferase may be any mutant in which amino acid sequence is mutated from the natural sequence by gene recombination technology. The luciferase may also be a domain that catalyzes luminescence of the native luciferase or its mutated protein. The luciferase is, for example, a luciferase (Oplophorus luciferase) derived from Oplophorus sp. (e.g., Oplophorus grachlorostris), a domain (19 kDa protein) that catalyzes luminescence of Oplophorus luciferase, a luciferase (Renilla luciferase) derived from Renilla sp. (e.g., Renilla reniformis or Renilla muelleri) and their mutated proteins. These luciferases and their mutated proteins (e.g., the protein of the present invention) can be produced by the method described in, e.g., Shimomura et al. (1988) Biochem. J. 251, 405-410, Shimomura et al. (1989) Biochem. J. 261, 913-920, or Shimomura et al. (1990) Biochem. J. 270, 309-312, or a modification thereof. Alternatively, as various products are commercially available from INC Corporation, Wako Pure Chemicals Industries, Promega Corporation, etc., these products may be used as well. The method for producing the protein of the present invention is as described hereinabove.

The apoprotein is as described above.

The luciferase, etc. used is preferably the 19 kDa protein of Oplophorus luciferase and its mutated proteins (e.g., the protein of the present invention), and more preferably, the protein of the present invention.

In Oplophorus luciferase, the nucleotide sequence and amino acid sequence of the 19 kDa protein of luciferase from Oplophorus grachlorostris are shown in SEQ ID NO: 8 and SEQ ID NO: 9, respectively.

Use of Reporter Protein as Luminescence Substrate

The coelenterazine analog of the present invention may also be used as a luminescence substrate for reporter proteins to determine the activity (transcription activity) of a sequence engaged in promoter regulation. The polynucleotide encoding the luciferase, etc. is fused to a target promoter or other expression control sequence (e.g., an enhancer, etc.) to construct a vector. The vector is transformed to a host cell. The coelenterazine analog of the present invention is brought in contact with the host cell. By detecting the luminescence from the luciferin, etc., the activity of the target promoter or other expression control sequence can be determined. As used herein, the term "contact" is intended to mean that a host cell and the coelenterazine analog of the invention are allowed to be present in the same culture system or reaction system, and includes, for example, the coelenterazine analog of the invention being added to a culture container charged with a host cell, a host cell being mixed with the coelenterazine analog of the invention, a host cell being cultured in the presence of the coelenterazine analog of the invention, and the like.

The luciferin, etc. is as described in the section entitled "Use of Detection Marker as Luminescence Substrate by Luminescence."

The luciferin used is preferably the 19 kDa protein of *Oplophorus* luciferase and its mutated proteins (e.g., the protein of the present invention), and more preferably, the protein of the present invention.

The polynucleotide of the present invention may preferably be used as a reporter gene, as described above.

Material for Amusement Supplies

The coelenterazine analog of the present invention can be advantageously used as a luminescence substrate when the luciferase, etc. is used as a luminescence substrate in materials for amusement supplies. Examples of the amusement supplies include luminescent bubble soap, luminescent ice, luminescent candies, luminescent paints, etc. The amusement supplies of the invention can be prepared in a conventional manner.

The luciferase, etc. used is preferably the 19 kDa protein of *Oplophorus* luciferase and its mutated proteins (e.g., the protein of the present invention), and more preferably, the protein of the present invention.

Bioluminescence Resonance Energy Transfer (BRET) Method

The coelenterazine analog of the present invention can be used as a luminescence substrate for the luciferase, etc., in the method of analyses such as an analysis of biological functions, measurement of enzyme activities, etc., based on the principle of intermolecular interactions by the bioluminescence resonance energy transfer (BRET) method.

For example, using the luciferase, etc. and the coelenterazine analog of the present invention as donors and a fluorescent substance (e.g., an organic compound or a fluorescent protein) as an acceptor, the interactions between the donors and acceptor can be detected by causing bioluminescence resonance energy transfer (BRET) between them.

In an embodiment of the present invention, the organic compound used as an acceptor is Hoechst 3342, Indo-1, DAPI, etc. In another embodiment of the present invention, the fluorescent protein used as an acceptor is a green fluorescent protein (GFP), a blue fluorescent protein (BFP), a mutant GFP fluorescent protein, phycobilin, etc.

In a preferred embodiment of the present invention, the physiological functions to be analyzed include an orphan receptor (in particular, a G-protein conjugated receptor), apoptosis, transcription regulation by gene expression, etc.

In a preferred embodiment of the present invention, the enzyme to be analyzed is protease, esterase, kinase, or the like.

Analysis of the physiological functions by the BRET method may be performed by publicly known methods, for example, by a modification of the method described in *Biochem. J.* 2005, 385, 625-637 or Expert Opin. Ther Tarets, 2007 11: 541-556. Assay for the enzyme activity may also be performed by publicly known methods, for example, by a modification of the method described in *Nature Methods* 2006, 3:165-174 or *Biotechnol J.* 2008, 3:311-324.

The luciferase, etc. used is preferably the 19 kDa protein of *Oplophorus* luciferase and its mutated proteins (e.g., the protein of the present invention), and more preferably, the protein of the present invention.

7. Kit of the Invention

The present invention also provides a kit comprising (i) the coelenterazine analog of the invention and (ii) at least one selected from the group consisting of the luciferase, etc., a polynucleotide encoding the luciferase, etc., a recombinant vector comprising the polynucleotide, and a transformant comprising the polynucleotide. A preferred embodiment of the present invention further provides a kit comprising (i) the coelenterazine analog of the invention and (ii) at least one selected from the group consisting of a luciferase, a polynucleotide encoding the luciferase, a recombinant vector comprising the polynucleotide, and a transformant comprising the polynucleotide.

The luciferase used is preferably the 19 kDa protein of *Oplophorus* luciferase and its mutated proteins (e.g., the protein of the present invention), and more preferably, the protein of the present invention.

The kit of the invention can be prepared by conventional methods using conventional materials. The kit of the invention may additionally comprise, for example, sample tubes, plates, instructions for the user, solutions, buffers, reagents, and either samples suitable for standardization or control samples. The kit of the invention may further comprise salts containing halide ions.

The kit of the present invention may be used for the aforesaid measurement using a reporter protein or a reporter gene, as a detection marker by luminescence, the analysis of physiological functions or enzyme activities by the BRET method, or the like. The kit may also be used for the luminescence method which will be later described.

8. Method for Luminescence Reaction

Luminescence Reaction

The luminescence reaction using the coelenterazine analog of the invention as a substrate can be performed by contacting the coelenterazine analog of the invention with luciferase. As used herein, the "contact" is intended to mean that the coelenterazine analog of the invention and luciferase are allowed to be present in the same reaction system, and includes, for example, the coelenterazine analog of the invention being added to a container charged with a luciferase, the luciferase being added to a container charged with the coelenterazine analog of the invention, and the coelenterazine analog of the invention being mixed with the luciferase. The reaction can be carried out under conditions conventionally used for the luminescence reaction using *Oplophorus* luciferase or under a modification of these conditions.

Specifically, solvents for the reaction which are employed are, for example, a buffer solution such as Tris-HCl buffer, sodium phosphate buffer, etc., water, and the like.

Temperatures for the reaction are generally at approximately 4° C. to 40° C. and preferably approximately 4° C. to 25° C.

In the reaction solution, pH is generally approximately 5 to 10, preferably approximately 6 to 9, more preferably approximately 7 to 8 and most preferably approximately 7.5.

The luciferase used is preferably the 19 kDa protein of *Oplophorus* luciferase and its mutated proteins (e.g., the protein of the present invention), and more preferably, the protein of the present invention.

The coelenterazine analog of the present invention may also be added to the reaction system in the form of a solution in a polar solvent such as dimethylformamide, dimethylsulfoxide, etc., or in an alcohol such as methanol, ethanol, butanol, etc.

Activation of Luminescence Activity

The luminescence activity of the protein of the invention wherein the luciferin serves as a substrate is activated by halide ions, non-ionic surfactants, etc.

Examples of the halide ions are fluorine ions, chlorine ions, bromine ions and iodine ions; preferred are chlorine ions, bromine ions and iodine ions.

The concentration of the halide ions is generally approximately 10 µM to 100 mM, preferably approximately 100 µM to 50 mM and particularly preferably approximately 1 mM to 20 mM.

To add the halide ions to the reaction system, there is a method which comprises adding these ions in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI KF, KCl, KBr, KI, $CaF_2$, $CaCl_2$, $CaBr_2$, $CaI_2$, $MgF_2$, $MgCl_2$, $MgBr_2$, $MgI_2$, etc.

Commercial products (trademark) of the non-ionic surfactants include Tween 20 (polyoxyethylene sorbitan monolaurate), Tween 80 (polyoxyethylene sorbitan monooleate), Triton X-100 (polyethylene glycol-p-isooctylphenyl ether), Briji-58 (polyoxyethylene (20) cetyl ether), Nonidet P-40 (ethylphenol poly(ethylene glycol ether)n), etc., and preferably, Tween 20, Triton X-100, etc.

The concentration of the non-ionic surfactants is generally approximately 0.0002% (w/v) to 0.2% (w/v), preferably approximately 0.001% (w/v) to 0.1% (w/v), and more preferably approximately 0.05% (w/v) to 0.02% (w/v).

All literatures and publications mentioned in this specification are herein incorporated in their entirety by reference into the specification, irrespective of their purposes.

Unless otherwise indicated with respect to the embodiments and working examples, the methods described in standard sets of protocols such as J. Sambrook, E. F. Fritsch & T. Maniatis (Ed.), Molecular cloning, a laboratory manual (3rd edition), Cold Spring Harbor Press, Cold Spring Harbor, N.Y. (2001); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., etc., or modifications or variations thereof are used. When commercially available reagent kits or measuring apparatuses are used, protocols attached thereto are used unless otherwise indicated.

The objects, characteristics, and advantages of the present invention as well as the idea thereof are apparent to those skilled in the art from the descriptions given herein. Based on the description given herein, those skilled in the art can easily work the present invention.

It is to be understood that the mode for carrying out the invention, specific working examples, etc. are to be taken as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to EXAMPLES below but is not deemed to limit the invention thereto.

Example 1

Synthesis of C6d-f-Coelenterazine

1) Synthesis of 1,1-Diethoxy-3-(4-fluorophenyl)propan-2-one

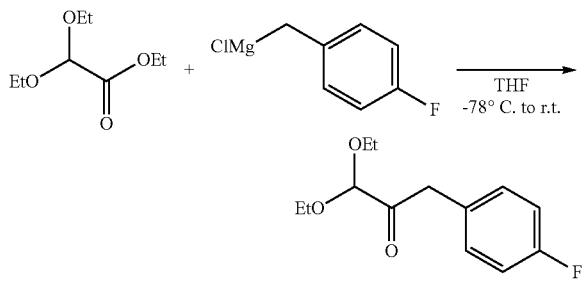

Under argon atmosphere, a diethyl ether solution of (4-fluorobenzyl)magnesium chloride (0.25 M, 20.0 mL, 5.0 mmol) was added slowly to a solution of ethyl diethoxyacetate (890 µL, 5.00 mmol) in tetrahydrofuran (THF) (50 mL) at −78° C. After stirring at −78° C. for 2 hours, the temperature was gradually elevated to room temperature, followed by stirring for 12 hours. To the mixture was added aqueous 20% ammonium chloride solution (10 mL). The mixture was extracted with ethyl acetate (×3). The organic layer was successively washed with water (×1) and brine (×1) and then dried over anhydrous sodium sulfate. After filtration, the filtrate was concentrated under reduced pressure and the residue was purified by silica gel flash column chromatography (n-hexane/ethyl acetate=19/1→4/1) to give 1,1-diethoxy-3-(4-fluorophenyl)propan-2-one as a colorless oily substance (622 mg, 2.59 mmol, 51.7%).

TLC $R_f$=0.24 (n-hexane/ethyl acetate=20/1);

$^1$H NMR (500 MHz, $CDCl_3$) δ 1.25 (t, 6H, J=7.0 Hz), 3.55 (dq, 2H, J=7.5, 9.5 Hz), 3.68 (dq, 2H, J=7.5, 9.5 Hz), 3.86 (s, 2H), 4.62 (s, 1H), 6.97-7.02 (m, 2H), 7.15-7.19 (m, 2H).

2) Synthesis of C6d-f-Coelenterazine (C6d-f-CTZ)

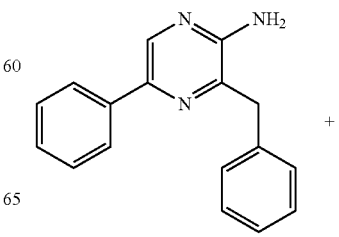

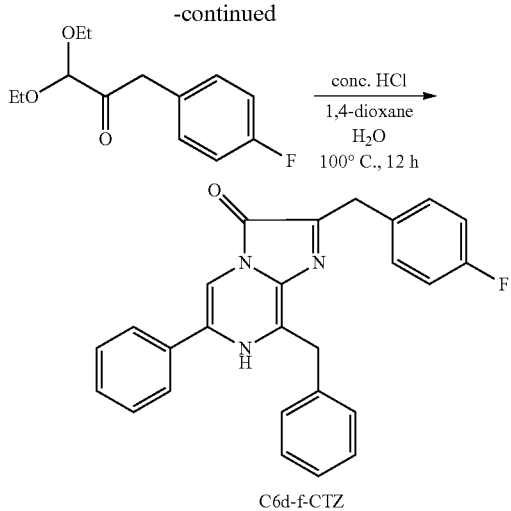

C6d-f-CTZ

Under argon atmosphere, 1,1-diethoxy-3-(4-fluorophenyl)propan-2-one (333 mg, 1.39 mmol) was dissolved in 1,4-dioxane (2.0 mL) and water (0.4 mL). To the solution was added 2-amino-3-benzyl-5-phenylpyrazine (261 mg, 1.00 mmol). After cooling to 0° C., conc. hydrochloric acid (0.20 mL) was added to the mixture, which was stirred at 100° C. for overnight (12 hours). The mixture was allowed to cool to room temperature and concentrated under reduced pressure. The residue was purified in an argon flow by silica gel flash column chromatography (n-hexane/ethyl acetate=5/1→1/1→ethyl acetate→ethyl acetate/methanol=50/1→20/1) to give the crude product (264 mg, <0.645 mmol) containing C6d-f-CTZ as a major compound. The resulting solid was further purified by reprecipitation (n-hexane/methanol) to give C6d-f-CTZ as a pale brown powder (49.2 mg, 120 μmol, 12.0%).

TLC $R_f$=0.35 (ethyl acetate);

$^1$H NMR (500 MHz, CD$_3$OD) δ 4.29 (s, 2H), 4.58 (s, 2H), 7.05-7.09 (m, 2H), 7.24-7.28 (m, 1H), 7.31-7.34 (m, 4H), 7.42 (d, 2H, J=7.0 Hz), 7.49-7.56 (m, 3H), 7.93 (br d, 2H, J=7.0 Hz), 8.54 (s, 1H).

Example 2

Design and Chemical Synthesis of Codon-Optimized Nucleic Acid

Based on the amino acid sequence (SEQ ID NO: 1) of the catalytic 19 kDa domain (sometimes referred to as "nanoLuc") of the mutated *Oplophorus* luciferase from Promega Corp., which was generated by mutagenesis of the catalytic 19 kDa domain (sometimes referred to as "KAZ") of native *Oplophorus* luciferase, a codon-optimized gene for the mutated catalytic 19 kDa domain (sometimes referred to as "nanoKAZ") of *Oplophorus* luciferase was designed. More specifically, the nucleotide sequence (SEQ ID NO: 2) of nanoKAZ was designed, without changing the amino acid sequence (SEQ ID NO: 1) of nanoLuc, using only the amino acid codon frequently used in human. The codon-optimized gene for the nanoKAZ domain was chemically synthesized in a conventional manner.

Example 3

Construction of Vector for Secretion and Expression of Codon-Optimized nanoKAZ Domain Protein Using Secretory Signal Sequence of *Gaussia* Luciferase in Cultured Animal Cells A vector for expression of the codon-optimized nanoKAZ domain protein was constructed as follows.

Firstly, a novel expression vector pcDNA3-GLsp in cultured animal cells was constructed (FIG. 1). Specifically, the secretory signal sequence of *Gaussia* luciferase was obtained from the pcDNA3-GLuc vector (manufactured by Prolume Ltd.) by PCR using the primer set of GLsp-1R/EcoRI (SEQ ID NO: 3: 5' ggc GAATTCGGT GGG CTT GGC CTC GGC CAC 3', EcoRI sequence underlined) and T7 primer (SEQ ID NO: 4: 5' TAATACG ACTCAC-TATAGGG 3') and digested with HindIII/EcoRI. The resulting fragment was inserted into the HindIII/EcoRI sites which are the restriction enzyme site of the pcDNA3 vector (manufactured by Invitrogen Corp.) to construct the novel expression vector of pcDNA3-GLsp. That is, the novel expression vector is under the control of the CMV promoter and has a Kozak sequence, followed by the secretory signal sequence of *Gaussia* luciferase and the multiple cloning site sequence.

Next, the codon-optimized nanoKAZ domain protein expression vector pcDNA3-GLsp-nanoKAZ (FIG. 2) was constructed as follows, using the novel expression vector pcDNA3-GLsp.

Figure 2:
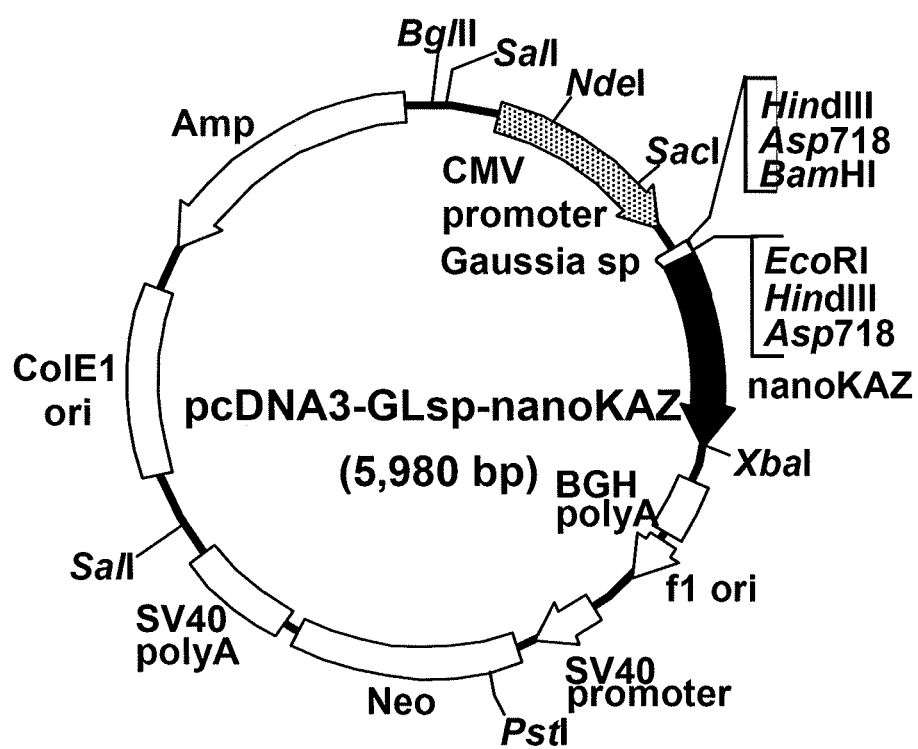
FIG. 2 shows a plasmid map of pcDNA3-GLsp-nanoKaz.

The gene fragment of the codon-optimized nanoKAZ domain was digested with the restriction enzyme of EcoRI/XbaI in a conventional manner and then was ligated to the EcoRI-XbaI site of pcDNA3-GLsp to construct the expression vector pcDNA3-GLsp-nanoKAZ, as shown in FIG. 2. The sequence of the inserted gene was confirmed by DNA sequencing using a DNA Sequencer (manufactured by ABI Co.).

The nucleotide sequence of GLsp-nanoKAZ encoded in the expression vector pcDNA3-GLsp-nanoKAZ is shown by SEQ ID NO: 5 and the amino acid sequence is shown by SEQ ID NO: 6. The amino acid sequence after secretion is shown by SEQ ID NO: 7.

Example 4

Transfection of Vector into Cultured Animal Cells and Preparation of Enzyme Used for Assay (1) Purification of Expression Plasmid Using the pcDNA3-GLsp-nanoKAZ plasmid obtained in EXAMPLE 3, the following experiment was performed. The pcDNA3-GLsp-nanoKAZ plasmid was purified in *Escherichia coli* JM83 strain by using a Plasmid Purification Kit (manufactured by QIAGEN, Inc.), and dissolved in sterile water to a concentration of 1 μg/μL.

(2) Transfection and Preparation of Enzyme for Assay

The Chinese hamster ovary-derived cell line CHO-K1 was cultured in Ham's F-12 medium (manufactured by Wako Pure Chemical Industries, Ltd.) containing 10% (v/v) calf fetal serum (manufactured by Biowest Inc.), and cultured in DMEM (manufactured by Wako Pure Chemical Industries, Ltd.) containing 10% (v/v) calf fetal serum (manufactured by Biowest Inc.). The respective cells were seeded in a 6-well culture plate (n=2) with $1\times10^5$ cells/well/2 mL medium, and cultured in an incubator at 37° C. in 5% $CO_2$, respectively. After 24 hours, the purified pcDNA3-GLsp-nanoKAZ plasmid was transfected into CHO-K1 cells using a FuGene HD Transfection Kit (manufactured by Promega Corp.), which was used in the subsequent experiment. Specifically, 1 µg of the pcDNA3-GLsp-nanoKAZ expression vector and 3 µL of FuGene HD were added to 100 µL of medium, which was allowed to stand at room temperature for 15 minutes. Then 100 µL of the DNA-FuGene complex solution was added to the cells in the 6 wells. After incubation for 48 hours, the culture medium was recovered and used as the secreted nanoKAZ enzyme solution for assay.

Example 5

Assay for Luminescence Activity in Codon-Optimized nanoKAZ Domain Protein Expressed in Cultured Animal Cells The enzyme solution, 5 µL, for assay obtained in EXAMPLE 4 (2) was added to 100 pt of 50 mM Tris-HCl (pH 7.6)-10 mM EDTA (Wako Pure Chemical Industries) containing 1 µg each of various coelenterazine analogs to initiate the luminescence reaction. The luminescence activity was determined by a luminometer (AB2200, manufactured by Atto Company) for 60 seconds and expressed by the maximum luminescence intensity ($I_{max}$) and the relative light units (du) of the luminescence intensity integrated for 60 seconds.

Example 6

Figure 3:
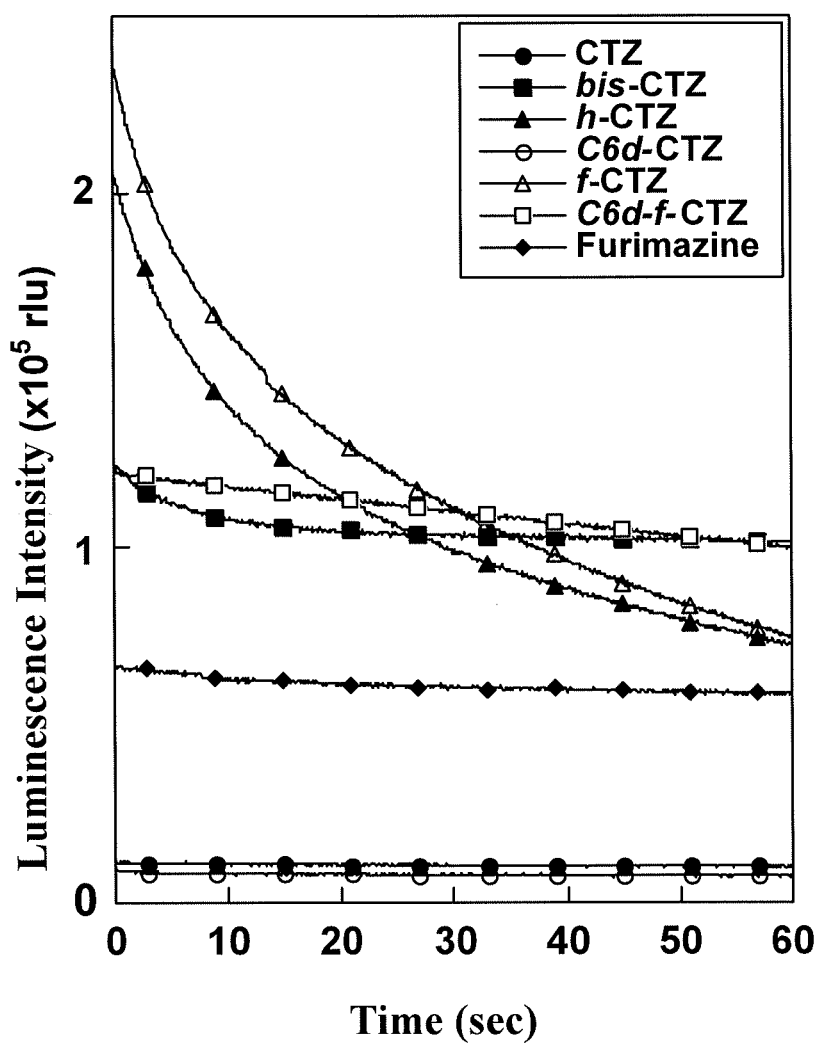
FIG. 3 shows the luminescence patterns of recombinant nanoKAZ with coelenterazine analogs by comparison to coelenterazines.

Substrate Specificity of Codon-Optimized nanoKAZ Domain Protein and Comparison of Luminescence Patterns The coelenterazine analogs used for substrate specificity analysis except for the analog described in EXAMPLE 1 were synthesized by the methods as described in the journals below, respectively. Specifically, bis-coelenterazine was synthesized by the method described in Nakamura et al. (1997) Tetrahedron Lett. 38: 6405-6406; Furimazine (Compound No. 3939 referred to in the journal) and C6d-coelenterazine (Compound No. 3840 referred to in the journal) by the method described in Hall et al. (2012) ACS Chem. Biol. 16: 848-1857; and the C2-coelenterazine analogs by the method described in Inouye et al (2010) Anal. Biochem. 407: 247-252. The enzyme solution of the culture medium in which nanoKAZ was secreted by the method as described in EXAMPLE 4 (2) was used for determining the luminescence activity with coelenterazine or its analogs. As a result, the substrate specificities for nanoKAZ are summarized in TABLE 1. In the coelenterazine analogs, the compounds exhibiting the relative maximum luminescence intensity 5 times or higher than that of coelenterazine were h-, bis-, and C6d-f-coelenterazines and furimazine, and the compounds exhibiting the relative amount of the integrated luminescence intensity for 1 min with 5 times or higher than that of coelenterazine were h-, f-, and C6d-f-coelenterazines. On the other hand, the luminescence patterns for these compounds are shown in FIG. 3. As shown in FIG. 3, bis-coelenterazine, furimazine and C6d-f-coelenterazine did not exhibit a rapid decay of the luminescence patterns. As a result, the luminescence substrates which can markedly improve the luminescence intensity and the amount of the integrated luminescence intensity to compare with furimazine are bis-coelenterazine and C6d-f-coelenterazine, showing a continuous luminescence without a decay of the luminescence intensity.

TABLE 1

Substrate Specificity of Codon-Optimized nanoKAZ Domain Protein

| Coelenterazine analog | Relative maximum luminescence intensity ($I_{max}$) | Relative amount of integrated luminescence intensity (1 min.) |
|---|---|---|
| Coelenterazine (CTZ) | 1.0 | 1.0 |
| C6d-Coelenterazine | 0.8 | 0.7 |
| h-Coelenterazine | 17.0 | 10.1 |
| bis-Coelenterazine | 10.3 | 9.7 |
| f-Coelenterazine | 19.5 | 11.1 |
| C6d-f-Coelenterazine | 10.1 | 10.1 |
| Furimazine | 5.5 | 5.7 |

Example 7

Substrate Specificity of Various Luciferases

The preparation of various luciferases and the determination of their luminescence activities were carried out in accordance with the methods as previously reported. The catalytic 19 kDa domain of *Oplophorus* luciferase was produced by the method described in Inouye S. & Sasaki S. (2007) Protein Express. Purif. 56, 261-268, *Gaussia* luciferase by the method described in Inouye S & Sahara Y. (2008) Biochem. Biophys. Res. Commun. 368, 600-605, *Renilla* luciferase and *Renilla* luciferase 547 by the method described in Inouye S. et al. (2013) Protein Express. Purif. 88, 150-156, and aequorin by the method described in Inouye S et al. (2010) Anal. Biochem. 407, 247-252, respectively, and used. The results of assay are shown in TABLE 2. Especially, novel C6d-f-coelenterazine was found to be a good substrate for the catalytic 19 kDa domain of *Oplophorus* luciferase.

TABLE 2

Substrate Specificities for Coelenterazine-type
Luciferases and Photoprotein

Maximum Luminescence Intensity (Imax, %)
(Relative Amount of Integrated
Luminescence Intensity (1 min, %))

| Coelenterazine analog | Catalytic 19 kDa domain of Oplophorus luciferase | Gaussia luciferase | Renilla luciferase | Renilla luciferase 547 | Aequorin |
|---|---|---|---|---|---|
| Coelenterazine (CTZ) | 100 (100) | 100 (100) | 100 (100) | 100 (100) | 100 (100) |
| C6d-Coelenterazine | 9.0 (7.7) | 0.8 (0.8) | 0.02 (0.02) | 0.12 (0.12) | 0.03 (0.03) |
| h-Coelenterazine | 92.6 (101) | 8.2 (12.1) | 68.5 (73.5) | 24.5 (16.4) | 84.0 (68.0) |
| bis-Coelenterazine | 108 (102) | 0 (0) | 0.04 (0.03) | 0.07 (0.08) | 0.01 (0.01) |
| f-Coelenterazine | 78.6 (85.7) | 5.0 (10) | 65.3 (71.4) | 78.0 (68.1) | 42.3 (59.0) |
| C6d-f-Coelenterazine | 100 (105) | 0 (0) | 0.07 (0.01) | 0.17 (0.13) | 0.12 (0.19) |
| Furimazine | 72.2 (65.2) | 0 (0) | 0.01 (0.01) | 0.01 (0.01) | 0.02 (0.02) |

Example 8

Evaluation of Stability of Coelenterazine Analogs in Aqueous Solution

The stability of coelenterazine analogs in an aqueous solution was examined by dissolving 10 μg of coelenterazine analogs in 0.5 mL of 30 mM Tris-HCl (pH 7.6), allowing the solution to stand at 37° C. for 22 hours, and then the degradation of coelenterazine analogs was determined by HPLC analysis. The HPLC analysis was performed by the modified method as described in Inouye S. et al. (2013) Protein Express. Purif. 88, 150-156.

The results are summarized in TABLE 3. After incubation for 22 hours, coelenterazine and furimazine were very unstable, and only 2% and 3% of undegraded compounds remained, respectively. On the other hand, 38% and 49% of bis-coelenterazine and C6d-f-coelenterazine remained, respectively. That is, it was found that C6d-f-coelenterazine was the most stable coelenterazine analog, indicating that the stability was markedly improved, by comparison to native coelenterazine.

TABLE 3

Comparison in Stability of Coelenterazine
Analog in Aqueous Solution

| Coelenterazine Analog | Incubation Time at 37° C. (hour) | Residual Ratio of Coelenterazine Analog (%) |
|---|---|---|
| Coelenterazine | 0 | 100 |
|  | 22 | 2 |
| bis-Coelenterazine | 0 | 100 |
|  | 22 | 38 |
| C6d-f- Coelenterazine | 0 | 100 |
|  | 22 | 49 |
| Furimazine | 0 | 100 |
|  | 22 | 3 |

SEQUENCE LISTING FREE TEXT

[SEQ ID NO: 1]
Amino acid sequence of nanoLuc and nanoKAZ.
[SEQ ID NO: 2]
Nucleotide sequence of the polynucleotide encoding nanoKAZ.
[SEQ ID NO: 3]
Nucleotide sequence of the primer used in EXAMPLE 3.
[SEQ ID NO: 4]
Nucleotide sequence of the primer used in EXAMPLE 3.
[SEQ ID NO: 5]
Nucleotide sequence of the polynucleotide encoding GLsp-nanoKAZ.
[SEQ ID NO: 6]
Amino acid sequence of GLsp-nanoKAZ.
[SEQ ID NO: 7]
Amino acid sequence of the secreted nanoKAZ
[SEQ ID NO: 8]
Nucleotide sequence encoding the 19 kDa protein of *Oplophorus grachlorostris* luciferase having the catalytic function of luminescence.
[SEQ ID NO: 9]
Amino acid sequence of the 19 kDa protein of *Oplophorus grachlorostris* luciferase having the catalytic function of luminescence.

The invention claimed is:

1. A compound represented by general formula (1) below:

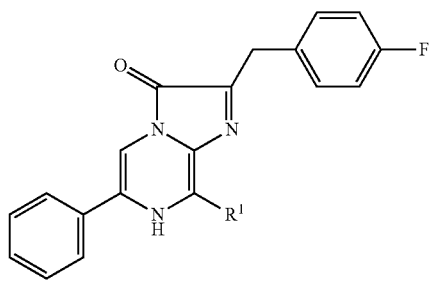

wherein in said general formula (1), $R^1$ is hydrogen, a substituted or unsubstituted aryl a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, or a heterocyclic group.

2. The compound of claim 1, wherein in said general formula (1), $R^1$ is phenyl, p-hydroxyphenyl, benzyl, α-hydroxybenzyl, p-hydroxybenzyl, phenylethyl, phenylvinyl, cyclopentyl, cyclopentylmethyl, cyclohexyl, cyclohexylmethyl, cyclohexylethyl, methyl, ethyl, propyl, 2-methylpropyl, 2-methylpropenyl, adamantylmethyl or thiophen-2-yl.

3. The compound of claim 2, wherein in said general formula (1), $R^1$ is benzyl, α-hydroxybenzyl or p-hydroxybenzyl.

4. The compound of claim 3, wherein in said general formula (1), $R^1$ is benzyl.

5. A method for producing a compound represented by general formula (1) below:

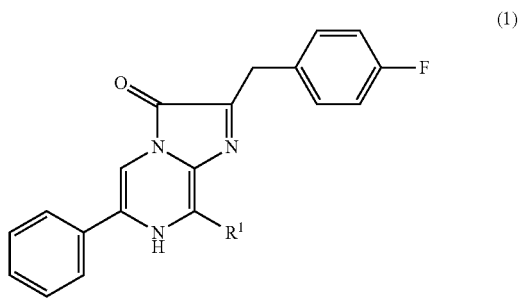

wherein in said general formula (1), $R^1$ is hydrogen, a substituted or unsubstituted aryl, a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, or a heterocyclic group; said method comprises reacting a compound represented by general formula (2) below:

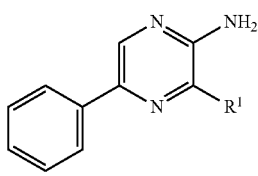

wherein in said general formula (2), R¹ is hydrogen, a substituted or unsubstituted aryl a substituted or unsubstituted arylalkyl, a substituted or unsubstituted arylalkenyl, an alkyl which may optionally be substituted with an alicyclic group, an alkenyl which may optionally be substituted with an alicyclic group, an alicyclic group, or a heterocyclic group; with a compound represented by general formula (3) below:

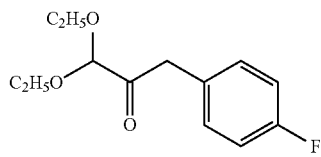

thereby producing said compound represented by general formula (1).

6. The method of claim 5, wherein in said general formula (1), R¹ is phenyl, p-hydroxyphenyl, benzyl, α-hydroxybenzyl, p-hydroxybenzyl, phenylethyl, phenylvinyl, cyclopentyl, cyclopentylmethyl, cyclohexyl, cyclohexylmethyl, cyclohexylethyl, methyl, ethyl, propyl, 2-methylpropyl, 2-methylpropenyl, adamantylmethyl or thiophen-2-yl.

7. The method of claim 6, wherein in said general formula (1), R¹ is benzyl, α-hydroxybenzyl or p-hydroxybenzyl.

8. The compound of claim 7, wherein in said general formula (1) R¹ is benzyl.

9. A kit comprising:
(i) the compound of claim 1; and,
(ii) a composition selected from the group consisting of a luciferase, a polynucleotide encoding the said luciferase, a recombinant vector comprising said polynucleotide encoding said luciferase, and a transformant comprising said polynucleotide encoding said luciferase.

10. The kit of claim 9, wherein said luciferase is a 19 kDa *Oplophorus* luciferase.

11. The kit of claim 9, wherein said luciferase is selected from the group consisting of (a), (b), and (c) below:
(a) a protein comprising the amino acid sequence of SEQ ID NO: 1,
(b) a protein comprising an amino acid sequence wherein 1 to 8 amino acids are deleted, substituted, inserted and/or added in the amino acid sequence of SEQ ID NO: 1 and having luminescence catalytic activity with luciferin as a substrate, and
(c) a protein comprising an amino acid sequence having at least 95% identity to the amino acid sequence of SEQ ID NO: 1 and having luminescence catalytic activity with luciferin as a substrate.

12. The kit of claim 9, wherein said polynucleotide encoding said luciferase is a polynucleotide selected from the group consisting of (a), (b), (c) and (d) below:

(a) a polynucleotide comprising the nucleotide sequence of SEQ ID NO: 2,
(b) a polynucleotide comprising a nucleotide sequence in which at least one nucleotide is deleted, substituted, inserted and/or added in the nucleotide sequence of SEQ ID NO: 2 and wherein said polynucleotide encodes a protein having luminescence catalytic activity with luciferin as a substrate,
(c) a polynucleotide comprising a nucleotide sequence having at least 90% identity to the nucleotide sequence of SEQ ID NO: 2 and wherein said polynucleotide encodes a protein having luminescence catalytic activity with luciferin as a substrate, and
(d) a polynucleotide comprising a polynucleotide that hybridizes under stringent conditions to a polynucleotide consisting of a nucleotide sequence complementary to the nucleotide sequence of SEQ ID NO: 2 and encodes a protein having luminescence catalytic activity with luciferin as a substrate.

13. A method for measuring luminescence contacting the compound of claim 1 with a luciferase.

14. The method of claim 13, wherein said luciferase is a 19 kDa *Oplophorus* luciferase.

15. The method of claim 13, wherein said luciferase is selected from the group consisting of (a), (b), and (c) below:
(a) a protein comprising the amino acid sequence of SEQ ID NO: 1,
(b) a protein comprising an amino acid sequence wherein 1 to 8 amino acids are deleted, substituted, inserted and/or added in the amino acid sequence of SEQ ID NO: 1 and having luminescence catalytic activity with luciferin as a substrate, and
(c) a protein comprising an amino acid sequence having at least 95% identity to the amino acid sequence of SEQ ID NO: 1 and having luminescence catalytic activity with luciferin as a substrate.

16. A method for assaying the activity of a target promoter comprising
providing a polynucleotide encoding a luciferase as a reporter gene and fusing said polynucleotide to said target promoter to construct a vector;
transforming said vector into a host cell;
contacting said host cell with the compound of claim 1; and
detecting luminescence, thereby assaying the activity of said target promoter.

17. The method of claim 16, wherein said luciferase encoded by said polynucleotide is a 19 kDa *Oplophorus* luciferase.

18. The method of claim 16, wherein said luciferase encoded by said polynucleotide is selected from the group consisting of (a), (b), and (c) below:
(a) a protein comprising the amino acid sequence of SEQ ID NO: 1,
(b) a protein comprising an amino acid sequence wherein 1 to 8 amino acids are deleted, substituted, inserted and/or added in the amino acid sequence of SEQ ID NO: 1 and having luminescence catalytic activity with luciferin as a substrate, and
(c) a protein comprising an amino acid sequence having at least 95% identity to the amino acid sequence of SEQ ID NO: 1 and having luminescence catalytic activity with luciferin as a substrate.

19. The method of claim 16, wherein the said polynucleotide encoding said luciferase is a polynucleotide selected from the group consisting of (a), (b), (c) and (d) below:

(a) a polynucleotide comprising the nucleotide sequence of SEQ ID NO: 2,
(b) a polynucleotide comprising a nucleotide sequence in which at least one nucleotide is deleted, substituted, inserted and/or added in the nucleotide sequence of SEQ ID NO: 2 and wherein said polynucleotide encodes a protein having luminescence catalytic activity with luciferin as a substrate,
(c) a polynucleotide comprising a nucleotide sequence having at least 90% identity to the nucleotide sequence of SEQ ID NO: 2 and wherein said polynucleotide encodes a protein having luminescence catalytic activity with luciferin as a substrate, and
(d) a polynucleotide comprising a polynucleotide that hybridizes under stringent conditions to a polynucleotide consisting of a nucleotide sequence complementary to the nucleotide sequence of SEQ ID NO: 2 and encodes a protein having luminescence catalytic activity with luciferin as a substrate.

* * * * *